United States Patent
Fichera et al.

(10) Patent No.: US 7,132,559 B2
(45) Date of Patent: Nov. 7, 2006

(54) NON-RACEMIC HEXAFLUOROLEUCINE, AND METHODS OF MAKING AND USING IT

(75) Inventors: Alfio Fichera, Malden, MA (US); Zihni Bilgicer, Somerville, MA (US); Krishna Kumar, Cambridge, MA (US); Xuechao Xing, Wilmington, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 10/468,574

(22) PCT Filed: Feb. 25, 2002

(86) PCT No.: PCT/US02/05386

§ 371 (c)(1),
(2), (4) Date: Mar. 15, 2004

(87) PCT Pub. No.: WO02/068592

PCT Pub. Date: Sep. 6, 2002

(65) Prior Publication Data

US 2004/0138493 A1 Jul. 15, 2004

Related U.S. Application Data

(60) Provisional application No. 60/348,091, filed on Oct. 29, 2001, provisional application No. 60/271,999, filed on Feb. 27, 2001.

(51) Int. Cl.
*C07C 327/30* (2006.01)
*C07C 237/20* (2006.01)

(52) U.S. Cl. .......................... 558/256; 560/19; 560/43; 560/47; 560/48; 560/155; 560/156; 560/172; 562/433; 562/456; 562/457; 562/553; 564/123; 564/163

(58) Field of Classification Search ................ 560/19, 560/43, 47, 48, 155, 172, 156; 562/433, 562/456, 457, 553; 564/123, 163; 558/256
See application file for complete search history.

(56) References Cited

U.S. PATENT DOCUMENTS

| | | | |
|---|---|---|---|
| 3,997,609 A | 12/1976 | Martini et al. | 260/584 C |
| 4,028,405 A | 6/1977 | Kollonitsch et al. | 260/534 C |
| 4,325,961 A | 4/1982 | Kollonitsch et al. | 424/273 R |
| 4,405,530 A | 9/1983 | Gerhart | 260/465.5 R |
| 4,418,077 A | 11/1983 | Bey et al. | 424/309 |
| 4,695,588 A | 9/1987 | Kollonitsch et al. | 514/538 |

OTHER PUBLICATIONS

CA:128:128262 abs of Helvetica Chimia Acta by Zhang et al 81(1) pp. 174-181, 1998.*
CA:120:123831 abs of Journal of Chromatography by Vlasakova et al 639(2) pp. 273-279, 1993.*
CA:87:68600 abs of Yuki Gosei Kagaku Kyokai Shi by Maki et al 34(10) pp. 722-725, 1976.*
Zhang et al., Asymmetric Synthesis of (S)-5,5,5,5', 5', 5'-Hexafluoroleucine, Jan. 1998, Helvetica Chimica Acta, vol. 81(1), pp. 174-181.*
Vlasakova et al., Insitute of Nuclear Biology and Radiochemistry, Czech Academy of Sciences, Videnska 1083, Prague, 14220/4, Czech., Journal of Chromatography (1993), 639(2), 273-9, CODEN: JOCRAM; ISSN: 0021-9673.
Zhang et al., Department Chemie Biochemie, Universtat Bern, Bern CH-3012, Switz., Helvetica Chimica Acta (1998), 81(1), 174-181, CODEN: HCACAV; ISSN: 0018-019X.
Maki et al., Ind. Res. Inst., Nagoya, Japan, Yuki Gosei Kagaku Kyokai Shi (1976), 34 (10), 722-5, CODEN: YGKKAE.
International Search Report, international application No. PCT/US02/05386.

* cited by examiner

*Primary Examiner*—Rosalynd Keys
(74) *Attorney, Agent, or Firm*—Dana M. Gordon; Foley Hoag LLP

(57) ABSTRACT

One aspect of the invention relates to hexafluoroleucine and congeners thereof, and methods of making the compounds. Another aspect of the nvention relates to the synthesis of protein cores comprising hexafluoroleucine and congeners thereof. Certain peptides comprising hexafluorleucine and congeners thereof have been characterized using comparative biophysical studies. In general, the fluorinated peptides show higher thermal stability and enhanced resistance to chemical denaturation. Further, mixed hydrocarbonfluorocarbon cores self-sort into homogeneous bundles, suggesting new avenues for the design and manipulation of protein-protein interfaces.

32 Claims, 15 Drawing Sheets

H: Ac-HN-CGGAQLKKELQALKKENAQLKWELQALKKELAQ-CO-NH$_2$
F: Ac-HN-CGGAQLKKELQALKKENAQLKWELQALKKELAQ-CO-NH$_2$

NON-RACEMIC HEXAFLUOROLEUCINE, AND METHODS OF MAKING AND USING IT

This application claims the benefit of priority to Patent Cooperation Treaty Application number PCT/US02/05386, filed Feb. 25, 2002; which claims the benefit of priority to U.S. Provisional Patent Application Ser. No. 60/271,999, filed Feb. 27, 2001; and U.S. Provisional Patent Application Ser. No. 60/348,091, filed Oct. 29, 2001.

BACKGROUND OF THE INVENTION

Proteins fold to adopt unique three dimensional structures, usually as a result of multiple non-covalent interactions that contribute to their conformational stability. Creighton, T. E. *Proteins: Structures and Molecular Properties;* 2nd ed.; W. H. Freeman: New York, 1993. Removal of hydrophobic surface area from aqueous solvent plays a dominant role in stabilizing protein structures. Tanford, C. *Science* 1978, 200, 1012–1018; and Kauzmann, W. *Adv. Protein Chem.* 1959, 14, 1–63. For instance, a buried leucine or phenylalanine residue can contribute ~2–5 kcal/mol in stability when compared to alanine. Although hydrogen bonds and salt bridges, when present in hydrophobic environments, can contribute as much as 3 kcal/mol to protein stability, solvent exposed electrostatic interactions contribute far less, usually 0.5 kcal/mol. Yu, Y. H.; Monera, O. D.; Hodges, R. S.; Privalov, P. L. *J. Mol. Biol.* 1996, 255, 367–372; and Lumb, K. J.; Kim, P. S. *Science* 1995, 268, 436–439. Hydrogen bonds between small polar side chains and backbone amides can be worth 1–2 kcal/mol, as seen in the case of N-terminal helical caps. Aurora, R.; Rose, G. D. *Protein Sci.* 1998, 7, 21–38. The energetic balance of these intramolecular forces and interactions with the solvent determines the shape and the stability of the fold.

While electrostatic interactions in designed structures can provide conformational specificity at the expense of thermodynamic stability, hydrophobic interactions afford a very powerful driving force for stabilizing structures. Recent studies have focused on the introduction of non-proteinogenic, fluorine containing amino acids as a means for increasing hydrophobicity, without significant concurrent alteration of protein structure. Bilgicer, B.; Fichera, A.; Kumar, K. *J. Am. Chem. Soc.* 2001, 123, 4393–4399; and Tang, Y.; Ghirlanda, G.; Vaidehi, N.; Kua, J.; Mainz, D. T.; Goddard, W. A.; DeGrado, W. F.; Tirrell, D. A. *Biochemistry* 2001, 40, 2790–2796. The estimated average volumes of $CH_2$ and $CH_3$ groups are 27 and 54 Å$^3$, respectively, as compared to the much larger 38 and 92 Å$^3$ for $CF_2$ and $CF_3$ groups. Israelachvili, J. N.; Mitchell, D. J.; Ninham, B. W. *Biochim. Biophysica Acta* 1977, 470, 185–201. Given that the hydrophobic effect is roughly proportional to the solvent exposed surface area, the large size and volume of trifluoromethyl groups, in combination with the low polarizability of fluorine atoms, results in enhanced hydrophobicity. Tanford, C. *The Hydrophobic Effect: Formation of Micelles and Biological Membranes;* 2d ed.; Wiley: New York, 1980. Indeed, partition coefficients point to the superior hydrophobicity of $CF_3$ (Π=1.07) over $CH_3$ (Π=0.50) groups. Resnati, G. *Tetrahedron* 1993, 49, 9385–9445. The low polarizability of fluorine also results in low cohesive energy densities of liquid fluorocarbons and is manifested in their low propensities for intermolecular interactions. Riess, J. G. *Colloid Surf.-A* 1994, 84, 33–48; and Scott, R. L. *J. Am. Chem. Soc.* 1948, 70, 4090–4093. These unique properties of fluorine simultaneously bestow hydrophobic and lipophobic character to biopolymers with high fluorine content. Marsh, E. N. G. *Chem. Biol.* 2000, 7, R153–R157.

Introduction of amino acids containing terminal trifluoromethyl groups at appropriate positions on protein folds increases the thermal stability and enhances resistance to chemical denaturants. Bilgicer, B.; Fichera, A.; Kumar, K. *J. Am. Chem. Soc.* 2001, 123, 4393–4399; and Tang, Y.; Ghirlanda, G.; Vaidehi, N.; Kua, J.; Mainz, D. T.; Goddard, W. A.; DeGrado, W. F.; Tirrell, D. A. *Biochemistry* 2001, 40, 2790–2796. Furthermore, specific protein-protein interactions can be programmed by the use of fluorocarbon and hydrocarbon side chains. Bilgicer, B.; Xing, X.; Kumar, K. *J. Am. Chem. Soc.* 2001, 123, 11815–11816. Because specificity is determined by the thermodynamic stability of all possible protein-protein interactions, a detailed fundamental understanding of the various combinations is essential.

The so-called "leucine zipper" protein motif, originally discovered in DNA-binding proteins but also found in protein-binding proteins, consists of a set of four or five consecutive leucine residues repeated every seven amino acids in the primary sequence of a protein. In a helical configuration, a protein containing a leucine zipper motif presents a line of leucines on one side of the helix. With two such helixes alongside each other, the arrays of leucines can interdigitate like a zipper and/or form side-to-side contacts, thus forming a stable link between the two helices. Moreover, an increase in the hydrophobicity of the leucine sidechains, e.g., by substitution of hydrogens with fluorines, in a leucine zipper motif should increase the strength of the zipper.

Selective fluorination of biologically active compounds is often accompanied by dramatic changes in physiological activities. (a) Welch, T.; Eswarakrishnan, S. *Fluorine in Bioorganic Chemistry;* Wiley-Interscience: New York, 1991 and references cited therein; (b) *Fluorine-containing Amino Acids;* Kukhar', V. P., Soloshonok, V. A., Eds.; John Wiley & Sons: Chichester, 1994; (c) Williams, R. M. *Synthesis of Optically Active α-Amino Acids,* Pergamon Press: Oxford, 1989; (d) Ojima, I.; Kato, K.; Nakahashi, K.; Fuchikami, T.; Fujita, M. *J. Org. Chem.* 1989, 54, 4511–4522; (e) Tsushima, T.; Kawada, K.; Ishihara, S.; Uchida, N.; Shiratori, O.; Higaki, J.; Hirata, M. *Tetrahedron* 1988, 44, 5375–5387; (f) Weinges, K.; Kromm, E. *Liebigs Ann. Chem.* 1985, 90–102; (g) Eberle, M. K.; Keese, R.; Stoeckli-Evans, H. *Helv. Chim. Acta* 1998, 81, 182–186; and (h) Tolman, V. *Amino Acids* 1996, 11, 15–36. Further, fluorinated amino acids have been synthesized and studied as potential inhibitors of enzymes and as therapeutic agents. Kollonitsch, J.; Patchett A. A.; Marburg, S.; Maycock, A. L.; Perkins, L. M.; Doldouras, G. A.; Duggan, D. E.; Aster, S. *D. Nature* 1978, 274, 906–908. Trifluoromethyl containing amino acids acting as potential antimetabolites have also been reported. (a) Walborsky, H. M.; Baum, M. E. *J. Am. Chem. Soc.* 1958, 80, 187–192; (b) Walborsky, H. M.; Baum, M.; Loncrini, D. F. *J. Am. Chem. Soc.* 1955, 77, 3637–3640; and (c) Hill, H. M.; Towne, E. B.; Dickey, J. B. *J. Am. Chem. Soc.* 1950, 72, 3289–3289.

We describe herein inter alia the design, synthesis, thermodynamic characterization and programmed self-sorting of peptide systems with orthogonally miscible hydrocarbon and fluorous, i.e., highly fluorinated cores.

SUMMARY OF THE INVENTION

A novel, short and efficient synthesis of (S)-5,5,5,5',5',5'-hexafluoroleucine (6) in greater than 99% ee starting from the protected oxazolidine aldehyde 1 is described. The enantiomeric excess of the product was calculated from an NMR analysis of a dipeptide formed by reaction with a protected L-serine derivative. Furthermore, a racemic sample of N-acylated hexafluoroleucine was enzymatically resolved by treatment with porcine kidney Acylase I and was found to have the same optical rotation as the sample of synthetic 6.

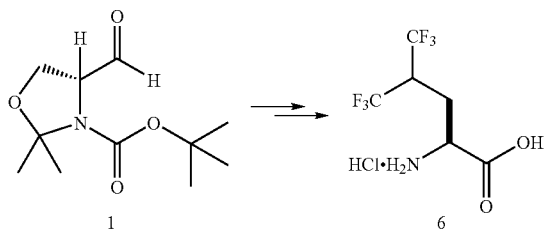

The invention also relates to a method for efficient resolution of the four diastereomers of 4,4,4-trifluorovaline and 5,5,5-trifluoroleucine. Appropriately derivatized trifluoroamino acids were separated by flash column chromatography into two enantiomeric pairs, which were further resolved by porcine kidney acylase I to deliver four pure diastereomers.

Another aspect of the present invention relates to the incorporation of hexafluoroleucine as a hydrophobic core residue in a designed coiled-coil, and tailored highly specific protein-protein interactions based on the substitution of a hydrophobic core of a protein with fluorinated residues. Another aspect of the invention relates to the design and manipulation of specific helix-helix interactions within the context of the nonpolar environment of membranes.

DETAILED DESCRIPTION OF THE INVENTION

Figure 13:
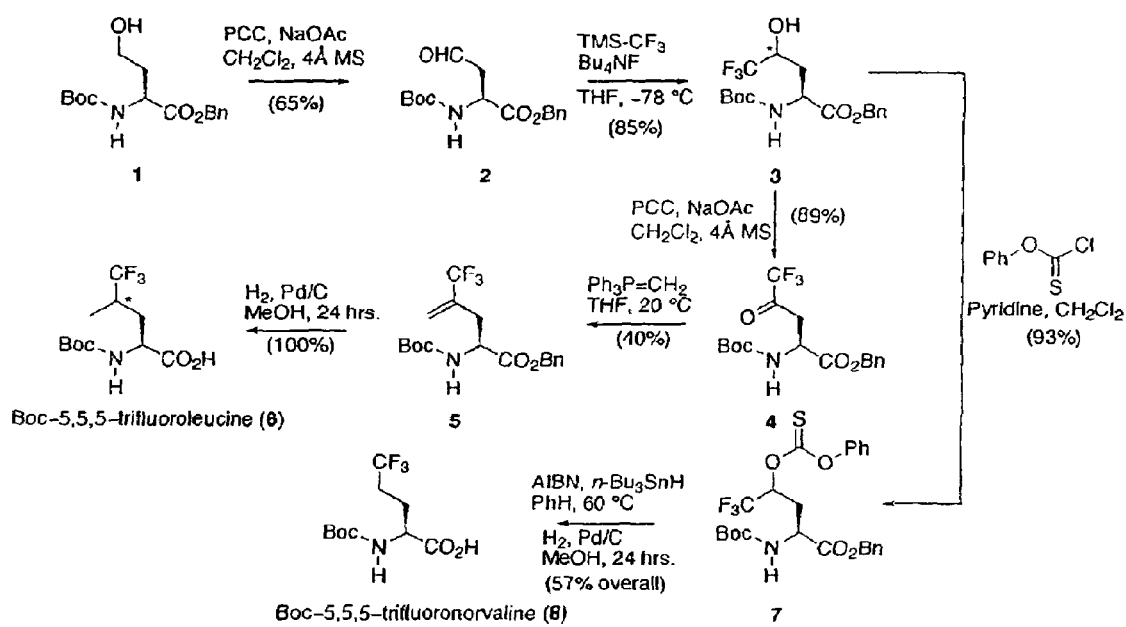
FIG. 13 depicts stereospecific syntheses of trifluoroleucine and trifluoronorvaline from L-homoserine (1). An asterisk indicates unresolved stereochemistry.
Figure 14:
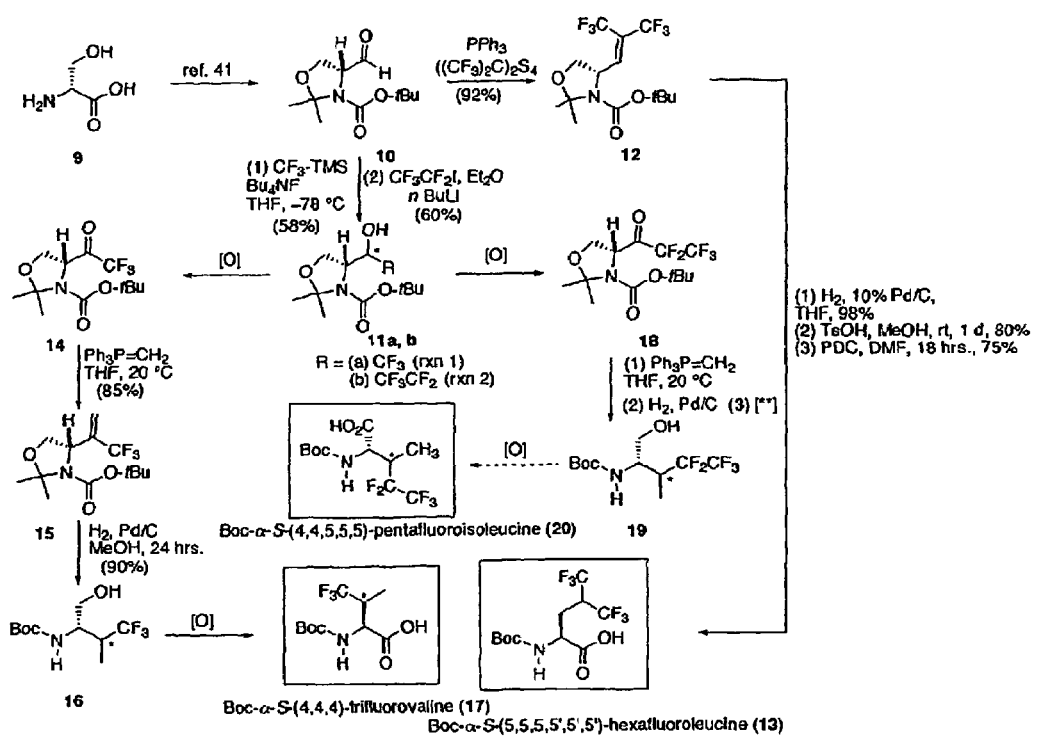
FIG. 14 depicts stereospecific syntheses of t-Boc-protected trifluorovaline, trifluoroisoleucine and hexafluoroleucine from oxazolidine aldehyde 10, derived from D-serine. [O]=PCC, NaOAc, 4 Å molecular sieves (yields range from 50–80%); [**] TsOH, MeOH, rt.
Figure 15:
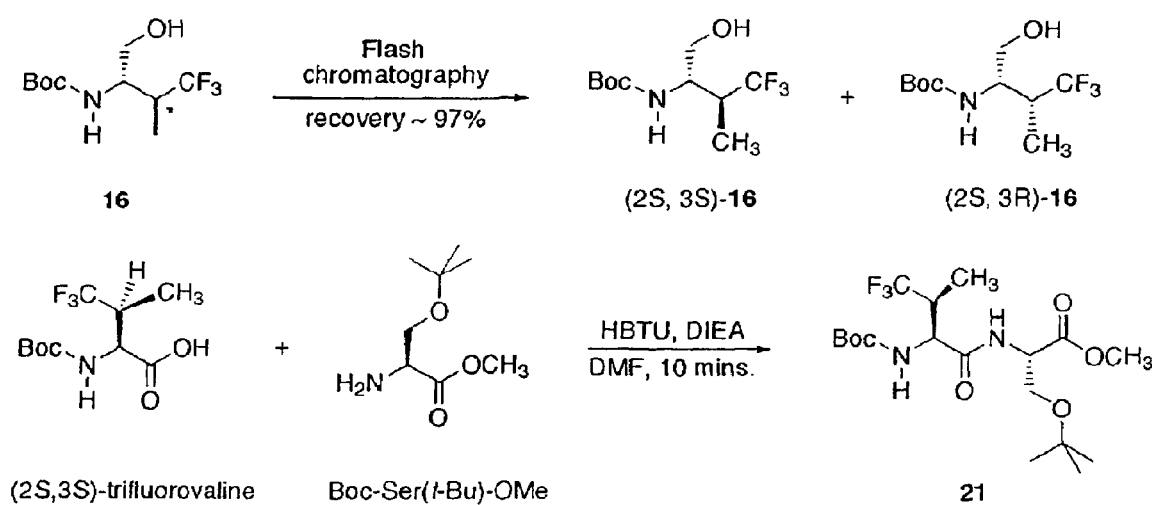
FIG. 15 depicts separation of diastereomeric alcohols 16 by flash column chromatography, followed by oxidation to give enantiomerically pure trifluorovalines. Comparison of the ¹H and ¹⁹F NMR spectra of dipeptide 21 to the corresponding dipeptide obtained from a mixture of (2S,3S)- and (2S,3R)-trifluorovaline shows that there has been no detectable racemization of 21.

General Synthesis of Trifluoromethyl Analogs of Leucine, Isoleucine, Valine and Norvaline We have invented methods to synthesize t-Boc protected trifluoroleucine, trifluorovaline, trifluoroisoleucine, hexafluoroleucine, and trifluoronorvaline, e.g., with α-S stereochemistry. Xing, X.; Fichera, A.; Kumar, K. "A novel synthesis of enantiomerically pure 5,5,5,5',5',5'-hexafluoroleucine." *Org. Lett.* 2001, 3, 1285–1286. These are derived from L-homoserine (FIG. 13) or D-serine (FIG. 14). An efficient synthesis of trifluoromethionine has been disclosed. Dannley, R. L.; Taborsky, R. G. "Synthesis of DL-S-trifluoromethylhomocysteine (trifluoromethylmethionine)." *J. Org. Chem.* 1957, 10, 1275–76; and Duewel, H.; Daub, E.; Robinson, V.; Honek, J. F. "Incorporation of trifluoromethionine into a phage lysozyrne: Implications and a new marker for use in protein F-19 NMR." *Biochemistry* 1997, 36, 3404–3416.

Suitably protected L-homoserine was oxidized to the corresponding aldehyde 2 followed by the fluoride-induced transfer of trifluoromethyl group from (trifluoromethyl)trimethylsilane. The resulting secondary fluoro alcohol 3 was oxidized with PCC in 89% yield and then subjected to Wittig olefination and catalytic hydrogenation to yield Boc-5,5,5-α-S-trifluorolecuine (6). The stereochemistry at the γ-position is 60% S and 40% R after the reduction reaction, and >99.5% S at the $C_\alpha$ position (ratios were determined by chiral HPLC). The diastereomerically pure compounds are obtained by reduction to the alcohol followed by chromatographic separation. Alcohol 3 was deoxygenated via homolytic reductive cleavage of its thionocarbonate intermediate (7), followed by catalytic reduction to remove the benzyl protecting functionality to yield Boc-5,5,5-α-S-trifluoronorvaline (8).

To install fluorinated side chains on other amino acids that are usually found in hydrophobic cores, we started with the oxazolidine aldehyde 10 (Garner aldehyde), available from D-serine in four steps (FIG. 14) which serves as a chiral non racemic synthon. Campbell, A. D.; Raynham, T. M.; Taylor, R. J. K. "A simplified route to the (R)-Garner aldehyde and (S)-vinyl glycinol." *Synthesis* 1998, 1707–1709; Garner, P.; Park, J. M. "The Synthesis and Configurational Stability of Differentially Protected Beta-Hydroxy-Alpha-Amino Aldehydes." *J. Org. Chem.* 1987, 52, 2361–2364; and Angrick, M. "Note On the Preparation of N-Substituted Aminoglyceraldehydes." *Mon. Chem.* 1985, 116, 645–649. At this stage, trifluoromethyl and pentafluoroethyl groups were introduced using methodology similar to that described earlier. The secondary alcohols were then oxidized to the corresponding ketones in good yield using PCC. The trifluoromethyl ketone 14 was further subjected to a Wittig olefination to yield alkene 15, which after catalytic hydrogenation and oxidation gave Boc-4,4,4-α-S-trifluorovaline (17). The pentafluoroethyl ketone 18 can be subjected to olefination under similar conditions followed by hydrogenation and oxidation to deliver Boc-5,5,5-trifluoroisoleucine (20). Aldehyde 10 is directly converted into the hexafluoro olefin 12 using the phosphonium analog of Middleton's phosphorane generated in situ from tetrakis(trifluoromethyl)-1,3-dithietane and triphenylphosphine. Catalytic hydrogenation was then used to unmask the alcohol and simultaneously reduce the alkene. The resulting alcohol was then oxidized using PCC to yield Boc-5,5,5,5',5',5'-α-S-hexafluoroleucine.

While the $C_\alpha$ stereochemistry is rigorously maintained throughout our synthetic scheme, the amino acids produced in this manner are still a mixture of isomers at the β-position in the case of trifluorovaline and trifluoroisoleucine. We have found that normal phase chromatography of alcohols 16 and 19 results in clean separation into the (2S,3S) and (2S,3R) components with recoveries in the 95–100% range. Furthermore, under standard peptide coupling conditions, the stereochemical integrity of the alpha carbon is not compromised.

Figure 12:
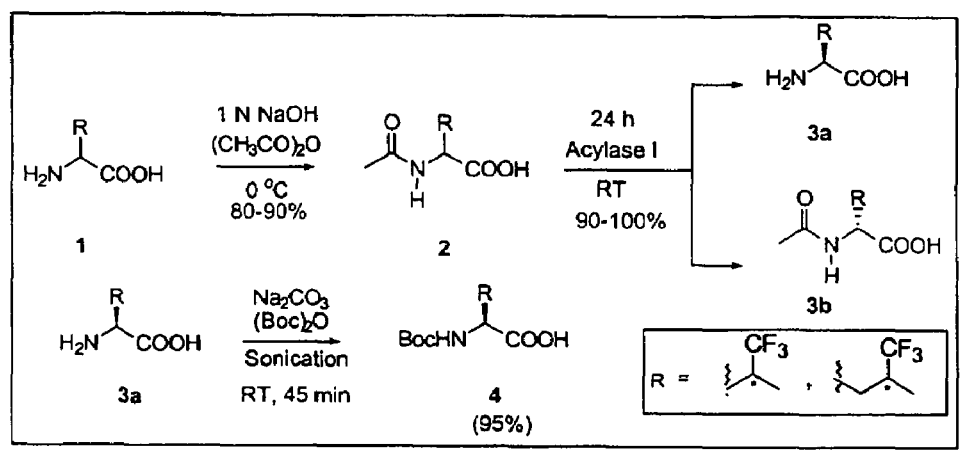
FIG. 12 depicts a method for the optical resolution of trifluoromethyl amino acids. The racemic mixture is N-acylated with acetic anhydride (90% yield), followed by enzymatic cleavage to yield the α-S isomer (99% yield). The stereochemistry at the β (trifluorovaline) and γ(trifluoroleucine) carbons is still unresolved. A method for the production of the N-t-Boc-protected amino acid is also depicted.

We have also taken advantage of enzymatic resolution of racemic amino acids with Acylase I and Lipase. Chenault, H. K.; Dahmer, J.; Whitesides, G. M. "Kinetic resolution of unnatural and rarely occurring amino acids: enantioselective hydrolysis of N-acyl amino acids catalyzed by acylase I." *J. Am. Chem. Soc.* 1989, 111, 6354–64; and Houng, J.-Y.; Wu, M.-L.; Chen, S.-T. "Kinetic resolution of amino acid esters catalyzed by lipases." *Chirality* 1996, 8, 418–422. Commercially available 5,5,5-trifluoroleucine and 4,4,4-trifluorovaline were acetylated with acetic anhydride and resolved (Acylase I) to yield the α-S amino acids (and >99.9% S stereochemistry at $C_\alpha$) in >90% yield. See FIG. 12; Tsushima, T.; Kawada, K.; Ishihara, S.; Uchida, N.; Shiratori, O.; Higaki, J.; Hirata, M. "Fluorine-containing amino acids and their derivatives. 7. Synthesis and antitumor activity of α- and γ-substituted methotrexate analogs." *Tetrahedron* 1988, 44, 5375; Lazar, J.; Sheppard, W. A. "Fluorinated analogs of leucine, methionine, and valine." *J. Med. Chem.* 1968, 11, 138; Watanabe, H.; Hashizume, Y.; Uneyama, K. "Homologation of trifluoroacetimidoyl iodides by palladium-catalyzed carbonylation. An approach to α-amino perfluoroalkanoic acids." *Tetrahedron Lett.* 1992, 33, 4333; Larsson, U.; Carlson, R.; Leroy, J. "Synthesis of amino acids with modified principal properties. 1. Amino acids with fluorinated side chains." *Acta Chem. Scand.* 1993, 47, 380–90; Ojima, I.; Kato, K.; Nakahashi, K.; Fuchikami, T.; Fujita, M. "New and effective routes to fluoro analogs of aliphatic and aromatic amino acids." *J. Org. Chem.* 1989, 54, 4511–22; Tolmann, V. "Syntheses of fluorinated amino acids. From the classical to the modern concept." *Amino Acids* 1996, 11, 15; Zhang, C.; Ludin, C.; Eberle, M. K.; Stoeckli-Evans, H.; Keese, R. "Asymmetric synthesis of (S)-5,5,5,5',5',5'-hexafluoroleucine." *Helv. Chim. Acta* 1998, 81, 174; Eberle, M. K.; Keese, R.; Stoeckli-Evans, H. "New synthesis and chirality of (−)-4,4,4,4',4',4'-hexafluorovaline." *Helv. Chim. Acta* 1998 81, 182; Keese, R.; Hinderling, C. "Efficient synthesis of (S)-methyl hexafluorovalinate." *Synthesis* 1996, 695; and Weinges, K.; Kromm, E. "Nonproteinogenic amino acids, II. Synthesis and determination of the absolute configuration of (2S,4S)-(−)- and (2S,4R)-(+)-5,5,5-trifluoroleucine." *Liebigs Ann. Chem.* 1985, 90–102. The selectivity of the acylase reaction was determined by chiral HPLC (CROWNPAK(+)-CR column, Daicel Chemical Industries). The trifluoro derivatives were further Boc protected under mild conditions without racemization for use in solid phase peptide synthesis (SPPS).

Stereochemistry at the β-carbon (trifluorovaline) and γ-carbon (trifluoroleucine) was left unresolved. In contrast, racemic hexafluorovaline resisted resolution by either Lipase or Acylase I.

Specific Synthesis of (S)-5,5,5,5',5'-Hexafluoroleucine

A novel, short and efficient synthesis of (S)-5,5,5,5',5',5'-hexafluoroleucine (6) in greater than 99% ee starting from the protected oxazolidine aldehyde 1 is described. The enantiomeric excess of the product was calculated from an NMR analysis of a dipeptide formed by reaction with a protected L-serine derivative. Furthermore, a racemic sample of N-acylated hexafluoroleucine was enzymatically resolved by treatment with porcine kidney Acylase I and was found to have the same optical rotation as the sample of synthetic 6.

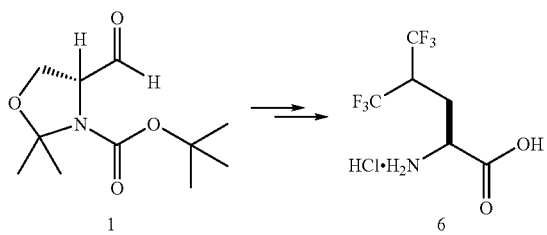

Herein, we disclose a novel and efficient synthesis of (S)-5,5,5,5',5',5'-hexafluoroleucine starting from commerically available D-serine. For synthesis of α-amino acids derived from D-serine using a serine aldehyde equivalent, see: Blaskovich, M. A.; Lajoie, G. A. *J. Am. Chem. Soc.* 1993, 115, 5021–5030. While there is one existing report of the synthesis of racemic hexafluoroleucine (Lazar, J.; Sheppard, W. A. *J. Med. Chem.* 1968, 11, 138), and another recent report detailing the preparation of 6 in 81% ee (Zhang, C.; Ludin, C.; Eberle, M. K.; Stoeckli-Evans, H.; Keese, R. *Helv. Chim. Acta* 1998, 81, 174–181), we have discovered a method to obtain hexafluoroleucine in>99% ee, e.g., for direct use in solid phase peptide synthesis.

Our synthesis commenced from the oxazolidine aldehyde 1 (Garner aldehyde) which served as a chiral, nonracemic synthon. See (a) Garner, P.; Park, J. M. *J. Org. Chem.* 1987, 52, 2361–2364. (b) Garner, P.; Park, J. M. *J. Org. Chem.* 1988, 53, 2979–2984. (c) Garner, P.; Park, J. M.; Malecki, E. *J. Org. Chem.* 1988, 53, 4395–4398. (d) Angrick, M. *Montash. Chem.* 1985, 116, 645–649. Aldehyde 1 is derived from D-serine and was obtained using a slight modification of a published procedure and is exceptionally stable towards racemization in subsequent steps. Campbell, A. D.; Raynham, T. M.; Taylor, R. J. K. *Synthesis* 1998, 1707–1709. In a key step, aldehyde 1 was converted to the bis-trifluoromethyl olefin 2 by a Wittig reaction in 92% yield (Scheme 1). See Korhummel, C.; Hanack, M. *Chem. Ber.* 1989, 122, 2187–2192.

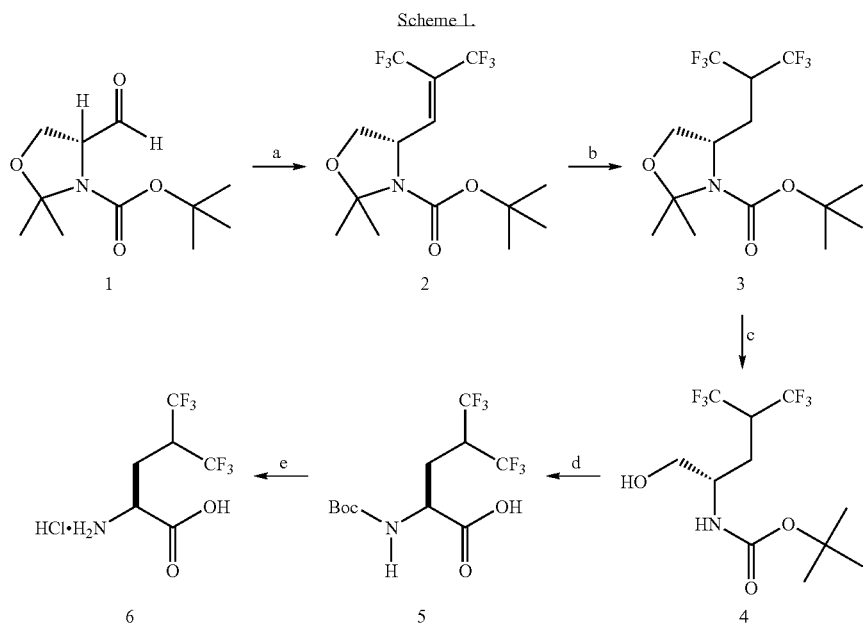

Reagents and conditions: (a) PPh₃, [(CF₃)₂C]₂S₂, Et₂O, -78° C. → rt, 3 d, 92%; (b) H₂, 10% Pd/C, THF, 98%; (c) TsOH, MeOH, rt, 1 d, 80%; (d) PDC, DMF, 18 hrs., 75%; (e) 40% CF₃CO₂H/CH₂Cl₂; HCl wash, 10 min., rt, >95%.

The ylide for this reaction is the phosphonium analog of Middleton's phosphorane, Middleton, W. J.; Sharkey, W. H. *J. Org. Chem.* 1965, 30, 1384, generated in situ from tetrakis(trifluoromethyl)-1,3-dithietane (Anello, L. G.; Vanderpuy, M. *J. Org. Chem.* 1982, 47, 377–378), and triphenyl phosphine. See (a) Burton, D. J.; Yang, Z. Y.; Qiu, W. M. *Chem. Rev.* 1996, 96, 1641–1715. (b) Dixon, D. A.; Smart, B. E. *J. Am. Chem. Soc.* 1986, 108, 7172–7177. (c) Burton, D. J.; Inouye, Y. *Tetrahedron Lett.* 1979, 3397–3400; and (d) Kobayashi, Y.; Nakajima, M.; Nakazawa, M.; Taguchi, T.; Ikekawa, N.; Sai, H.; Tanaka, Y.; Deluca, H. F. *Chem. Pharm. Bull.* 1988, 36, 4144–4147. The olefin 2 was reduced by catalytic hydrogenation over Pd/C to give the suitably substituted oxazolidine 3 in 98% yield. Next, the oxazolidine was subjected to acid catalyzed ring cleavage unmasking the alcohol 4. Alcohol 4 was oxidized to the carboxylic acid 5 using pyridinium dichromate and in the final step, the t-butyloxycarbonyl group was removed using trifluoroacetic acid to yield the hydrochloride salt of the desired α-amino acid 6. While the last deprotection step was carried out in order to verify the optical purity of 6, the Boc protected amino acid 5 could be directly used for solid phase synthesis of peptides.

The optical purity of synthetic 6 was verified in two ways. A racemic sample of 5 (prepared using a different route) and 5 obtained through the scheme described here were separately coupled to a protected methyl ester of L-serine (7), and the resulting dipeptide was analyzed using $^1$H NMR spectroscopy.

7

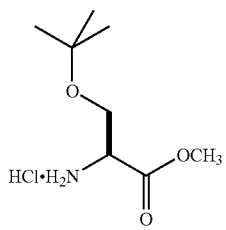

In the case of the dipeptide obtained from racemic 5, three signals corresponding to the t-Boc group, the methyl ester and the t-butyl ether were split into two peaks, presumably due to formation of two diastereomers; whereas, 5 from the present synthesis yielded a dipeptide with only one set of signals for the same three sets of protons. Further, racemic 6 was N-acylated and enzymatically resolved using porcine kidney Acylase I [E.C.N. 3.5.1.14] to yield the α-S isomer exclusively. See (a) Chenault, H. K.; Dahmer, J.; Whitesides, G. M. *J. Am. Chem. Soc.* 1989, 111, 6354–64; and (b) Fu, S. C. J.; Birnbaum, S. M. *J. Am. Chem. Soc.* 1953, 75, 918–920. The optical rotation of 6 obtained in this manner and that of the synthetic sample were identical. Thus, the synthesis proceeds in greater than >99% ee. The NMR data for 6 agree with those reported previously. Moreover, both the synthetic sample and the enzyme resolved samples of 6 had $[\alpha]^{260}_D$=+5.6° (c 1, CH$_3$OH). Likewise, the construction of 5,5,5,5',5',5'-(R)-hexafluoroleucine was achieved from L-senne.

Resolution of the Diastereomers of 4,4,4-Trifluorovaline and 5,5,5-Trifluoroleucine Reported here is an efficient resolution of the four diastereomers of 4,4,4-trifluorovaline (TFV) and 5,5,5-trifluoroleucine (TFL). The method as outlined in Scheme 1 is simple and practical. Appropriately derivatized TFL and TFV could be separated into two enantiomeric pairs by flash column chromatography. Subsequent enzymatic deacylation of the N-acetyl enantiomeric pairs of amino acids with porcine kidney acylase I delivers all four diastereomers in optically pure form. Chenault, H. K.; Dahmer, J.; Whitesides, G. M. *J. Am. Chem. Soc.* 1989, 111, 6354–6364.

Scheme 1

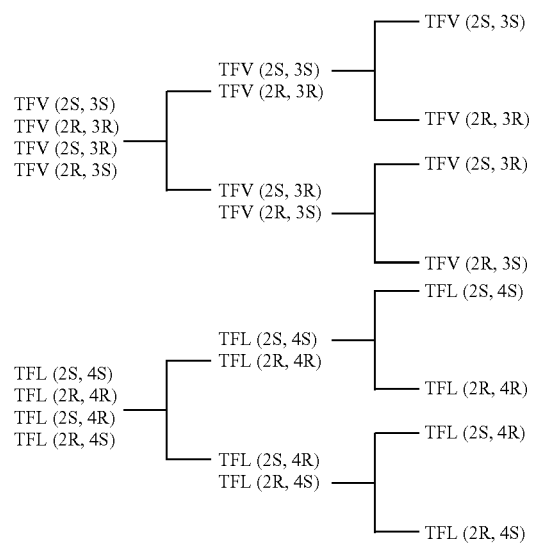

In the course of our study on the synthesis of enantiomerically pure TFV, we found that Boc-protected 4,4,4-trifluorovalinol α-S diastereomers could be easily separated by column chromatography on silica gel. This finding encouraged us to develop a resolution scheme for racemic TFV and TFL. As shown in Scheme 2, Boc-TFV 1 was first converted to Boc-trifluorovalinol 2 via esterification of 1 with methyl iodide, followed by reduction of the methyl ester with sodium borohydride in methanol in 73% overall yield for the two steps. The racemic mixture of trifluorovalinols was easily separated into the two enantiomeric pairs 2a [(2S,3S)+(2R,3R)] and 2b [(2S,3R)+(2R,3S)] by column chromatography on silica gel using n-pentane/ethyl ether (1:1) as eluant. Although the methyl esters of Boc-TFV 1 are also separable, they are not stable toward racemization in the subsequent reduction step. Oxidation of the hydroxyl group of 2a and 2b with PDC in DMF, removal of the Boc-protecting group with 30% trifluoroacetic acid in methylene chloride followed by acylation of the free amino group afforded the N-acetyl amino acids 3a and 3b respectively. Finally, enzymatic deacylation of 3a and 3b with porcine kidney acylase I afforded the four diastereomers 4a–d. Only those diastereomers that had an S configuration at $C_\alpha$ were deacylated by the enzyme. Removal of the acetyl group from the two $C_\alpha$-R diastereomers was realized by refluxing with 3 N HCl.

Scheme 2

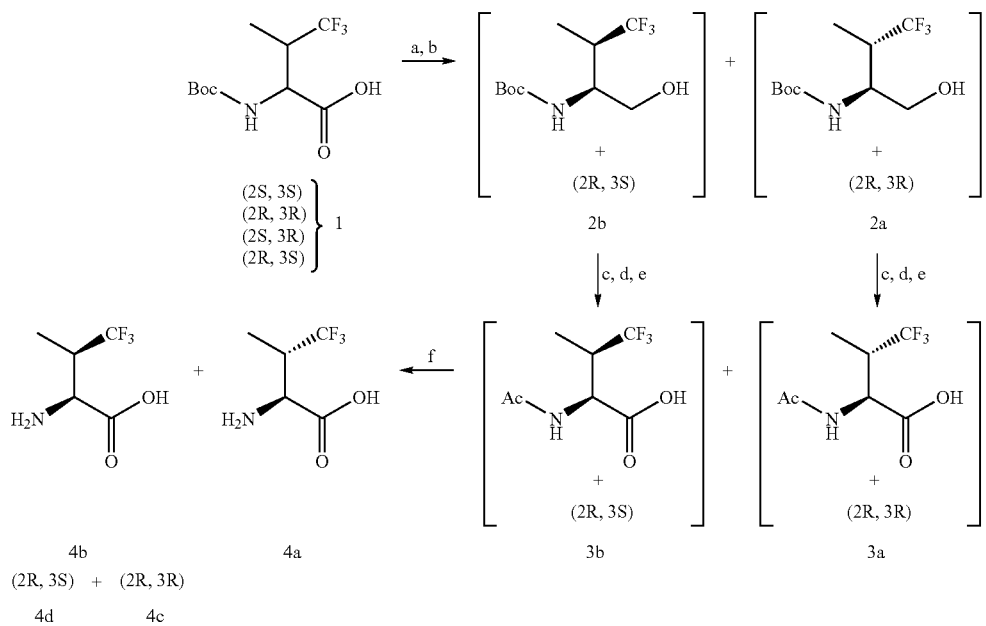

Reagents and conditions: (a) NaHCO₃, CH₃I, DMF, rt, 95%; (b) NaBH₄, CH₃OH, 77%; flash column chromatography, n-pentane/Et₂O (1:1), silica gel:2 (300:1); (c) PDC, DMF, rt, 65%; (d) 30% CF₃CO₂H/CH₂Cl₂, 100%; (e) NaOH/H₂O, Ac₂O, 0° C., 95%; (f) Porcine kidney acylase I, pH 7.50, 25° C., 95%; (g) 3N HCl, 98%.

Reagents and conditions: (a) NaHCO₃, CH₃I, DMF, rt, 95%; (b) NaBH₄, CH₃OH, 77%; flash column chromatography, n-pentane/Et₂O (1:1), silica gel:2 (300:1); (c) PDC, DMF, rt, 65%; (d) 30% CF₃CO₂H/CH₂Cl₂, 100%; (e) NaOH/H₂O, Ac₂O, 0° C., 95%; (f) Porcine kidney acylase I, pH 7.50, 25° C., 95%; (g) 3N HCl, 98%.

This strategy was also applied to the resolution of TFL (Scheme 3). Initially, Boc-TFL 5 was also converted to the corresponding alcohols following the procedure used for Boc-TFV 1, but we found that the trifluoroleucinols were not separable by column chromatography on silica gel. Interestingly, the methyl esters of 5 were readily separated into two pairs 6a and 6b on silica gel using n-pentane/ethyl ether (3:1) as eluant and were stable toward racemization in the reduction step. The N-acetyl amino acids 7a and 7b were obtained from 6a and 6b respectively by straightforward functional group transformations, which included reduction of the methyl ester group to hydroxyl, oxidation of the hydroxyl to acid, and replacement of the Boc-protecting group with an acetyl group. In the final step, enzymatic deacylation was applied to 7a and 7b to give diastereomerically pure compounds 8a–d.

Scheme 3

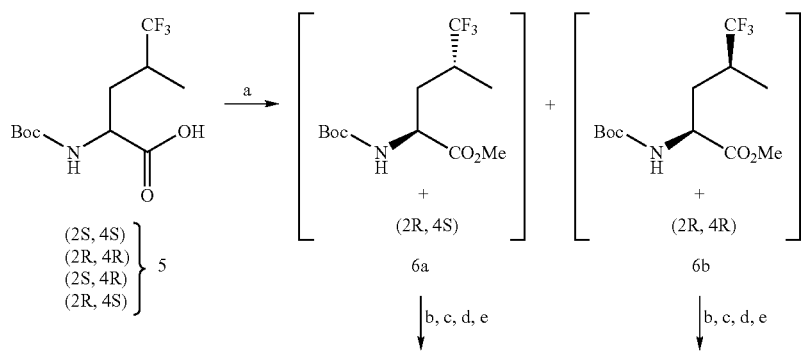

-continued

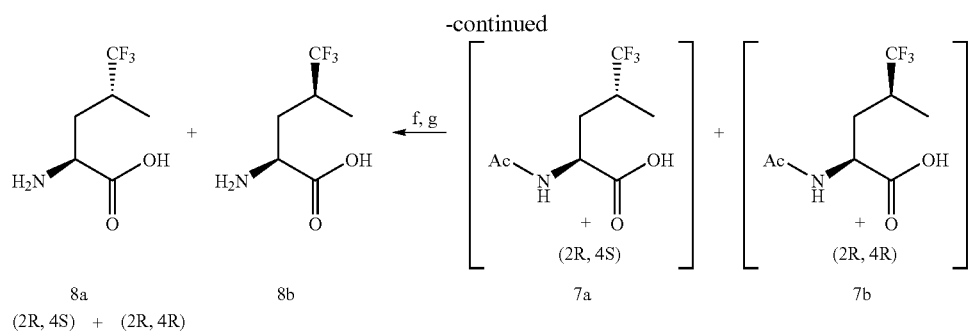

8a          8b          7a          7b
(2R, 4S) + (2R, 4R)
8c     8d

Reagents and conditions: (a) NaHCO$_3$, CH$_3$I, DMF, rt, 95%; flash column chromatography, n-pentane/Et$_2$O (4:1), silica gel:6 (400:1); (b) NaBH$_4$, CH$_3$OH, (94%; (c) PDC, DMF, rt, 60%; (d) 30% CF$_3$CO$_2$H/CH$_2$Cl$_2$, 100%; (e) NaOH/H$_2$O, Ac$_2$O, 0° C., 95%; (f) Porcine kidney acylase I, pH 7.5, 25° C., 95%; (g) 3N HCl, 96%.

The purity of the intermediates and the final diastereomers was ascertained using $^1$H, $^{13}$C and $^{19}$F NMR spectroscopy. The $^{19}$F NMR technique is particularly useful in this case for purity control due to its high sensitivity and the large chemical shift dispersion observed for these compounds. The enantiomeric pairs exhibited baseline separated $^{19}$F NMR spectra in each case. Contamination by the other enantiomeric pair or racemization during chemical transformation could be easily detected. The optical purity of the products was also verified by NMR analysis of dipeptides formed by coupling with a side chain protected methyl ester of L-serine. Xing, X.; Fichera, A.; Kumar, K. Org. Lett. 2001, 3, 1285–1286. The $^{19}$F NMR spectra clearly showed four peaks for dipeptides derived from the racemic mixture, two peaks for dipeptides derived from enantiomeric pairs, and only one peak for the diastereomerically pure dipeptide.

Programmed Sel-Sorting of Coiled Coils with Leucine and Hexafluoroleucine Cores

The coiled coil motif offers an excellent model system to explore specificity in protein-protein interactions. Lupas, A. Curr. Opin. Struct. Biol. 1997, 7, 388–393; and Lupas, A. Trends Biochem. Sci. 1996, 21, 375–382. These protein interaction motifs represent small, synthetically tractable targets for testing hypothetical constructs. Lajmi, A. R.; Lovrencic, M. E.; Wallace, T. R.; Thomlinson, R. R.; Shin, J. A. J. Am. Chem. Soc. 2000, 122, 5638–5639. The α-helical coiled coil is typically composed of a number of parallel or antiparallel α-helices wrapped around one another with a shallow left-handed superhelical twist. Crick, F. H. C. Acta Crystallographica 1953, 6, 689–697. They contain a heptad repeat, whose positions are denoted a–g, where the a and d positions are hydrophobic residues that form the interface between helices, and constitute the primary driving force for oligomerization. Additionally, interhelical electrostatic interactions between e and g residues provide a secondary source of stability. Monera, O. D.; Zhou, N. E.; Kay, C. M.; Hodges, R. S. J. Biol. Chem. 1993, 268, 19218–19227; and Monera, O. D.; Kay, C. M.; Hodges, R. S. Biochemistry 1994, 33, 3862–3871. From the crystal structures of 32-residue synthetic coiled coils, it is estimated that nearly 900 Å$^2$ surface area per helix is buried at a dimeric interface and nearly 1640 Å$^2$ per helix in a tetramer. Harbury, P. B.; Zhang, T.; Kim, P. S.; Alber, T. Science 1993, 262, 1401–1407; and O'Shea, E. K.; Klemm, J. D.; Kim, P. S.; Alber, T. Science 1991, 254, 539–544. The importance of hydrophobic surface area for coiled coil stability has been extensively studied through the use of de novo designed synthetic peptide models. Zhu, B. Y.; Zhou, N. E.; Kay, C. M.; Hodges, R. S. Protein Sci. 1993, 2, 383–394; and Zhu, B. Y.; Zhou, N. E.; Semchuk, P. D.; Kay, C. M.; Hodges, R. S. Int. J. Pept. Protein Res. 1992, 40, 171–179. These interaction surfaces are therefore ideally suited to study the effect of fluorination on the driving force and specificity.

Peptides were synthesized by the in situ neutralization protocol for t-Boc synthesis on 0.40 mmol NH$_2$ eq g$^{-1}$ methylbenzhydrylamine (MBHA) resin. At the end of linear synthesis, the formyl protecting group on the tryptophan residue was removed by treatment with 1:10 piperidine in DMF solution at 0° C. for 2 hrs. Further treatment with anhydrous HF resulted in the simultaneous removal of all side-chain protecting groups and cleavage of the peptide chain from the resin. The peptides were purified on reversed-phase HPLC using a linear gradient of acetonitrile in 0.1% trifluoroacetic acid (TFA)/water. The analytical purity of the peptides was confirmed by HPLC, amino acid analysis and MALDI mass spectrometry.

The disulfide bonded dimers of H (HH), F (FF) and the mixed dimer HF were synthesized by two different methods. The homodimers HH and FF were synthesized by overnight air oxidation of the monomeric peptides in 6 M guanidine hydrochloride (Gdn HCl) at pH 8.50 (50 mM Tris). The heterodimer HF was synthesized by reaction of H with a large excess of Ellman's reagent (ER, CAS No. 69-78-3) to produce an activated disulfide species at pH 7.50, followed by reaction with excess monomeric F at pH 5.10. Riddles, P. W.; Blakeley, R. L.; Zemer, B. Methods Enzymol. 1983, 91, 49–60. The resulting heterodimer HF was purified by reversed-phase HPLC.

Peptides H and F are equipped with N-terminal cysteine residues and were designed to form parallel homodimeric coiled coil assemblies. Wolf, E.; Kim, P. S.; Berger, B. Protein Sci. 1997, 6, 1179–1189. These peptides have an identical sequence except that all seven of the core leucine residues in H have been replaced by 5,5,5,5',5',5'-α-S-hexafluoroleucine in F, shielding 28 trifluoromethyl groups from aqueous solvent in the canonical fluorinated dimer.

Figure 1:
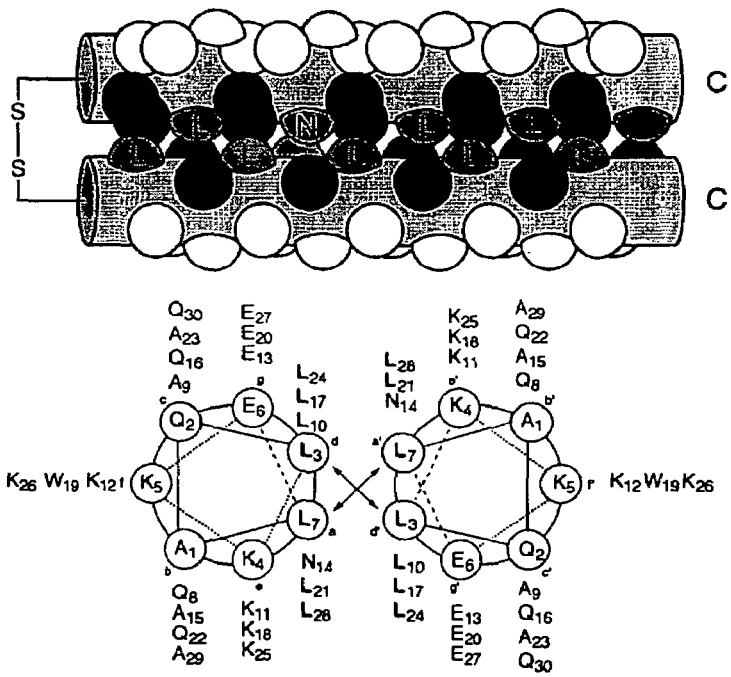
FIG. 1 depicts helical wheel representation of residues 1–30 of H and F looking down the superhelical axis from the N-terminus. All seven core leucines in H were replaced by hexafluoroleucine (L) in F.
Figure 1:
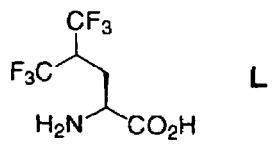

FIG. 1. Hexafluoroleucine was synthesized according to the procedure described herein. Xing, X.; Fichera, A.; Kumar, K. Org. Lett. 2001, 3, 1285–1286. The peptides were assembled on 4-methylbenzhydrylamine (MBHA) resin according to the in situ neutralization protocol for t-Boc peptide synthesis, as described previously, and purified by reverse-phase HPLC. Schnolzer, M.; Alewood, P.; Jones, A.; Alewood, D.; Kent, S. B. Int. *J. Pept. Protein Res*. 1992, 40, 180–193. Purity of the peptides was confirmed by analytical HPLC and MALDI mass spectrometry. H and F are designed to form parallel coiled coil structures due to unfavorable interhelical electrostatic interactions in the antiparallel arrangements. See Lumb, K. J.; Kim, P. S. *Biochemistry* 1995, 34, 8642–8648; and Harbury, P. B.; Zhang, T.; Kim, P. S.; Alber, T. *Science* 1993, 262, 1401–1407. Furthermore, a single polar residue, Asn14, which can only hydrogen bond in the parallel arrangement, was incorporated in the hydrophobic core. See Oakley, M. G.; Kim, P. S. *Biochemistry* 1998, 37, 12603–12610; and McClain, D. L.; Woods, H. L.; Oakley, M. G. *J. Am. Chem. Soc*. 2001, 123, 3151–3152. The peptides were equipped with a Gly-Gly-Cys tripeptide at the $NH_2$-terminus. The cysteine residue permits redox chemistry in the form of disulfide-thiol equilibrium, and the two glycine residues provide a flexible linker. Disulfide bonded dimers of H (HH) and F (FF) were synthesized by air oxidation of the monomeric peptides in pH 8.50 Tris buffer.

Figure 2:
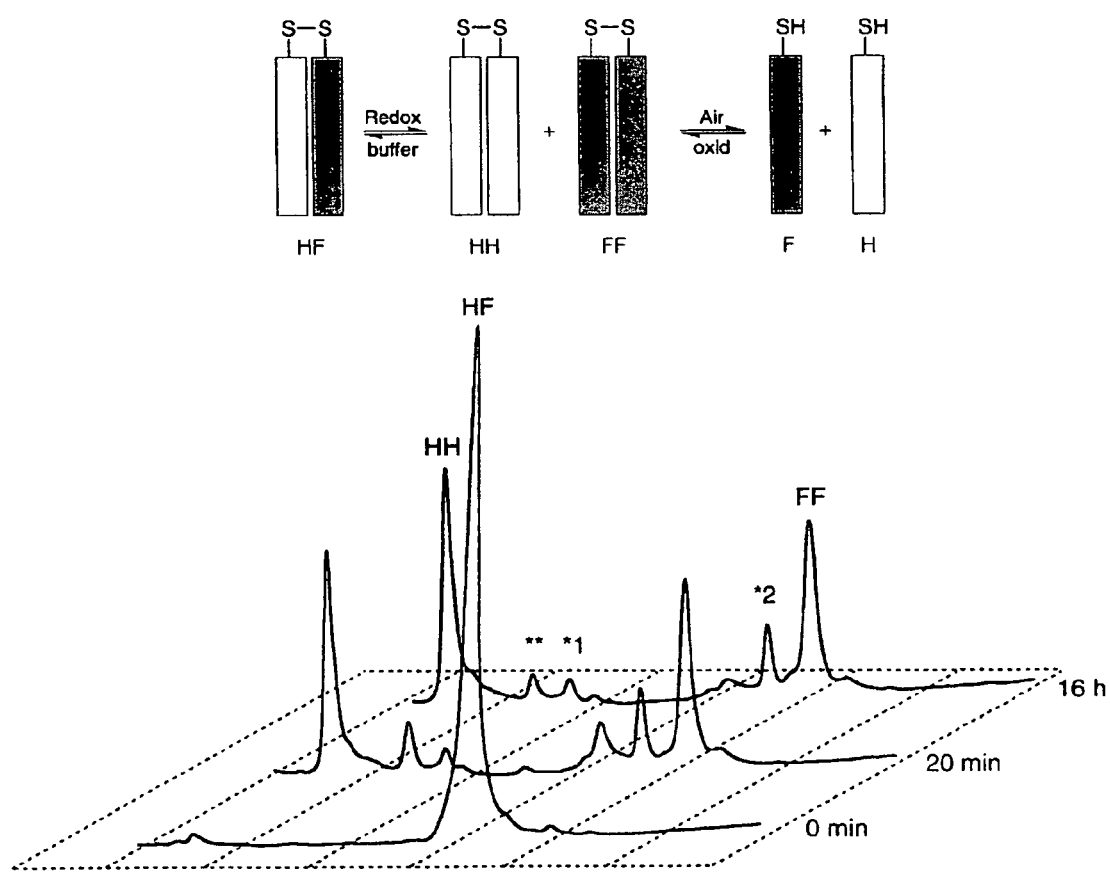
FIG. 2 depicts HPLC traces establishing preferential homodimer formation by fluorous and hydrocarbon cores. Preformed disulfide bonded heterodimer HF (20 μM) was incubated in redox buffer (125 μM oxidized glutathione, 500 μM reduced glutathione, pH 7.50, 100 mM NaCl, 200 mM MOPS). After 200 minutes, only homodimers and mixed disulfides remain. The mixed heterodimer is estimated to be less than 2% of all H— and F-containing peptides at equilibrium. Peaks marked "*1" and "*2" are H monomer and F-glutathione mixed disulfide, respectively, and the peak marked "**" is an impurity. The equilibrium lies firmly in favor of the homodimers HH and FF. The free energy of specificity for formation of homodimers, $\Delta G_{spec}$=–2.1 kcal/mol.

The extent of the preference for sorting into homodimeric populations under equilibrium conditions was examined by a disulfide exchange assay. See Harbury, P. B.; Kim, P. S.; Alber, T. *Nature* 1994, 371, 80–83; Oakley, M. G.; Kim, P. S. *Biochemistry* 1998, 37, 12603–12610; and Saghatelian, A.; Yokobayashi, Y.; Soltani, K.; Ghadiri, M. R. *Nature* 2001, 409, 797–80. Preformed disulfide bonded heterodimer HF was incubated in a pH 7.50 redox buffer at 20° C., conditions under which disulfide exchange is rapid. Aliquots were removed from the reaction at various times and quenched with 5% trifluoroacetic acid. The time points were then analyzed by analytical reversed-phase HPLC. Relative concentrations of the disulfide bonded hetero- and homodimers were estimated by integration of the area under corresponding peaks at 230 nm. Within 30 minutes of the start of the reaction, the heterodimer disproportionates into the two homodimers HH and FF. Specifically, we observed about 10% of the H-gluathione and 20% of the F-glutathione disulfide adducts. Coincidentally, the H-glutathione disulfide co-eluted with HH. After 200 minutes, only a trace of the heterodimer (~3%) remains. FIG. 2. Further change in the reaction mixture was not observed even after 18 hours. Assuming that the glycyl linkers allow the cysteines to exchange randomly under redox buffer conditions, the data indicate that the homodimers are preferred over the heterodimer by 26-fold. In order to establish that the reaction had reached equilibrium, we placed an equimolar amount of the reduced peptides H and F under similar redox buffer conditions, and monitored the reaction for 18 hours. Again, the heterodimer accounted for only 3% of all disulfide bonded species. Unambiguous stepwise synthesis of the heterodimer HF confirms that the disulfide bond forming chemistry is reversible and under thermodynamic control, and that there are no kinetic barriers to the formation of the disulfide bonded heterodimer HF. The heterodimer HF was synthesized by reaction of H with Ellman's reagent to produce an activated disulfide species. This mixed disulfide was then reacted with excess monomeric F to yield HF. See Riddles, P. W.; Blakeley, R. L.; Zemer, B. *Methods Enzymol*. 1983, 91, 49–60.

Accordingly, peptides H and F are predisposed to form homodimers. See Otto, S.; Furlan, R. L. E.; Sanders, J. K. M. *J. Am. Chem. Soc*. 2000, 122, 12063–12064; Hioki, H.; Still, W. C. *J. Org. Chem*. 1998, 63, 904–905; and Rowan, S. J.; Hamilton, D. G.; Brady, P. A.; Sanders, J. K. M. *J. Am. Chem. Soc*. 1997, 119, 2578–2579. The relative instability of the heterodimer and the hyperstability of the fluorinated dimer provide the driving force for preferential homodimer formation. From the peak ratios at equilibrium, the free energy of specificity for the formation of homodimers, $\Delta G_{spec}$, is calculated to be at least −2.1 kcaumol. See Example 11.

TABLE 1

Melting temperatures and solution MWs for disulfide bonded dimers.

| Peptide | $T_m$ (° C.)[a] | $MW_{app}$ (no. of helices)[c] |
|---------|-----------------|-------------------------------|
| HH      | 34              | 7501 ± 38 (2)                 |
| HF      | 36              | 8815 ± 63[d] (2)              |
| FF      | 82 (45[b])      | 17835 ± 75 (4)                |

[a]Determined by monitoring the molar ellipticity at 222 nm as a function of temperature. Conditions: 2 μM peptide conc.; pH 7.40, 5 M Gdn HCl, 10 mM PBS.
[b]In 7 M Gdn HCl, pH 7.40, 10 mM PBS.
[c]Determined by sedimentation equilibrium. Conditions: 15 μM peptide conc., pH 7.40, 10 mM PBS, 10° C.
[d]Non random residuals.

Figure 3:
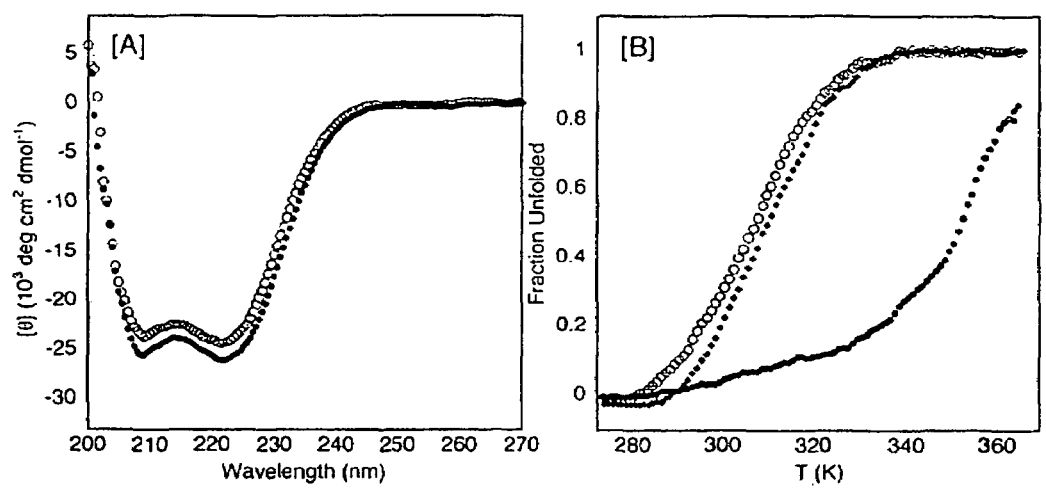
FIG. 3 depicts: [A] circular dichroism spectra of HH (○) and FF (●) (conditions: [HH]=[FF]=2 μM, pH 7.40, 137 mM NaCl, 2.7 mM KCl, 10 mM PBS, 10° C.); and [B] thermal denaturation profiles of HH (○), FF (●) and HF (♦) (conditions: [HH]=[FF]=[HF]=2 μM, 5 M Gdn HCl, pH 7.40, 137 mM NaCl, 2.7 mM KCl, 10 mM PBS).
Figure 4:
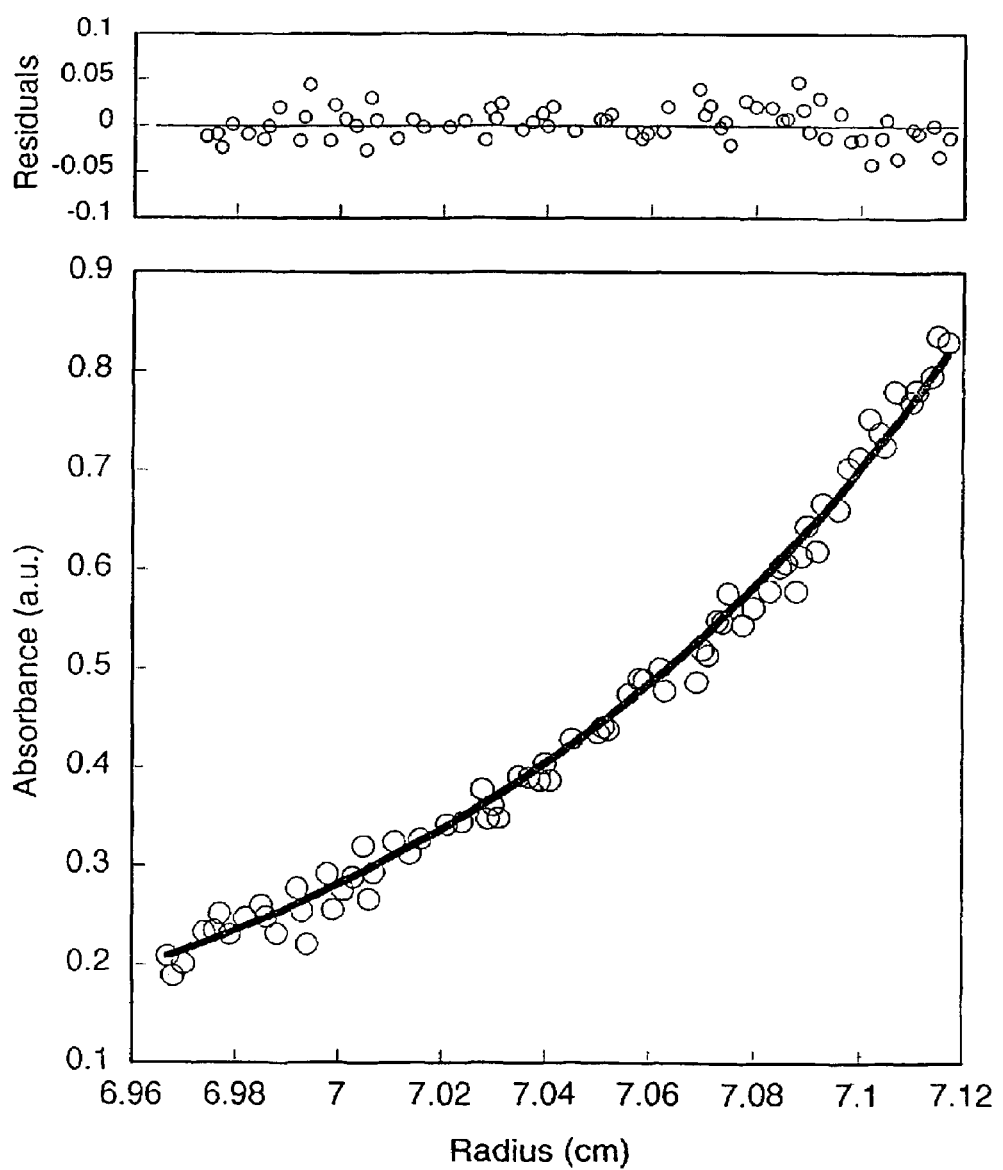
FIG. 4 depicts a representative sedimentation equilibrium trace for FF from analytical ultracentrifugation (conditions: 15 μM peptide (FF) conc., pH 7.40, 10 mM phosphate (pH 7.40), 137 mM NaCl, 2.7 mM KCl. Centrifugation: 26 000 rpm, 18 hours equilibration time, 10° C. $MW_{calc}$ (for dimer of FF)=18132, $MW_{found}$=17385).
Figure 5:
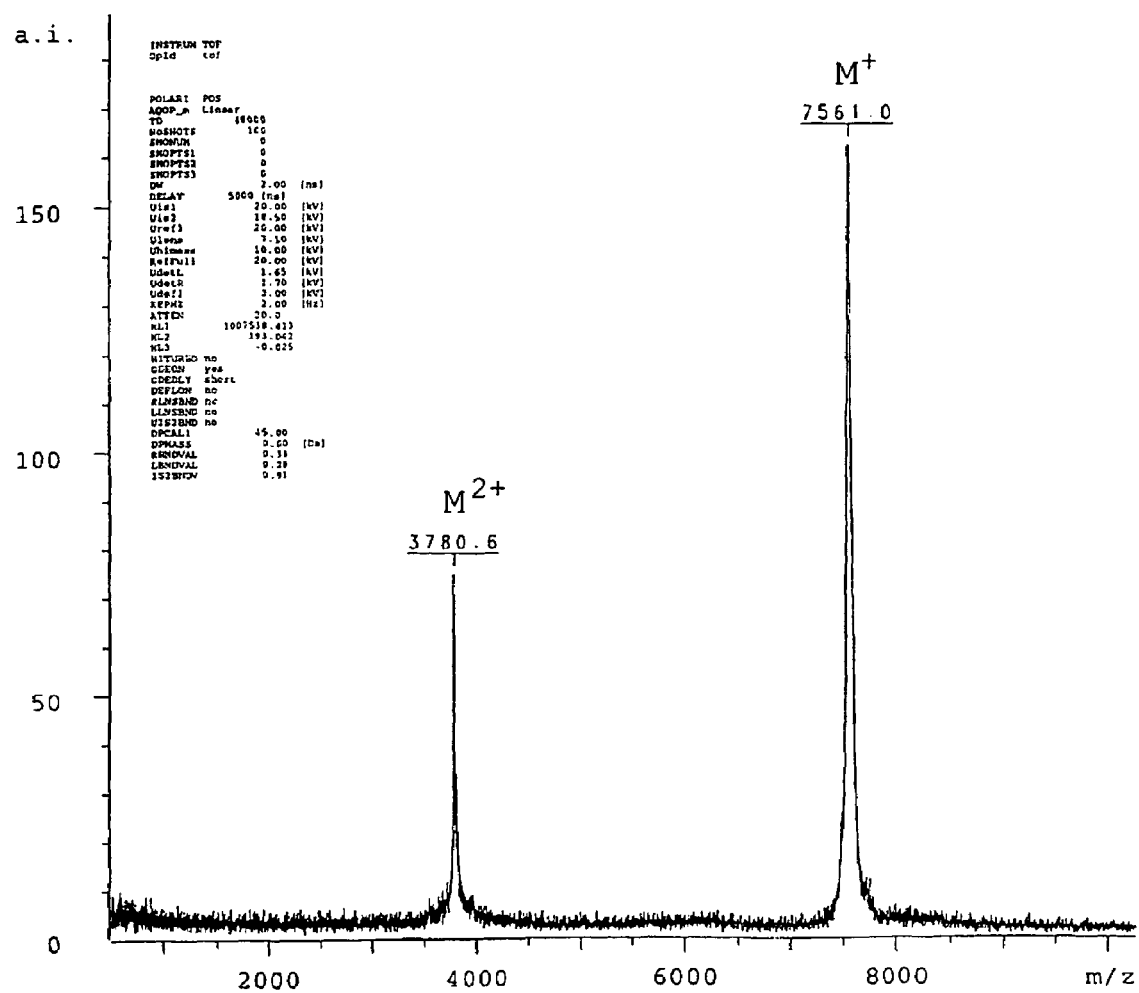
FIG. 5 depicts a MALDI mass spectrum of purified peptide HH (calcd. =7556.8 [M+], found=7561).
Figure 6:
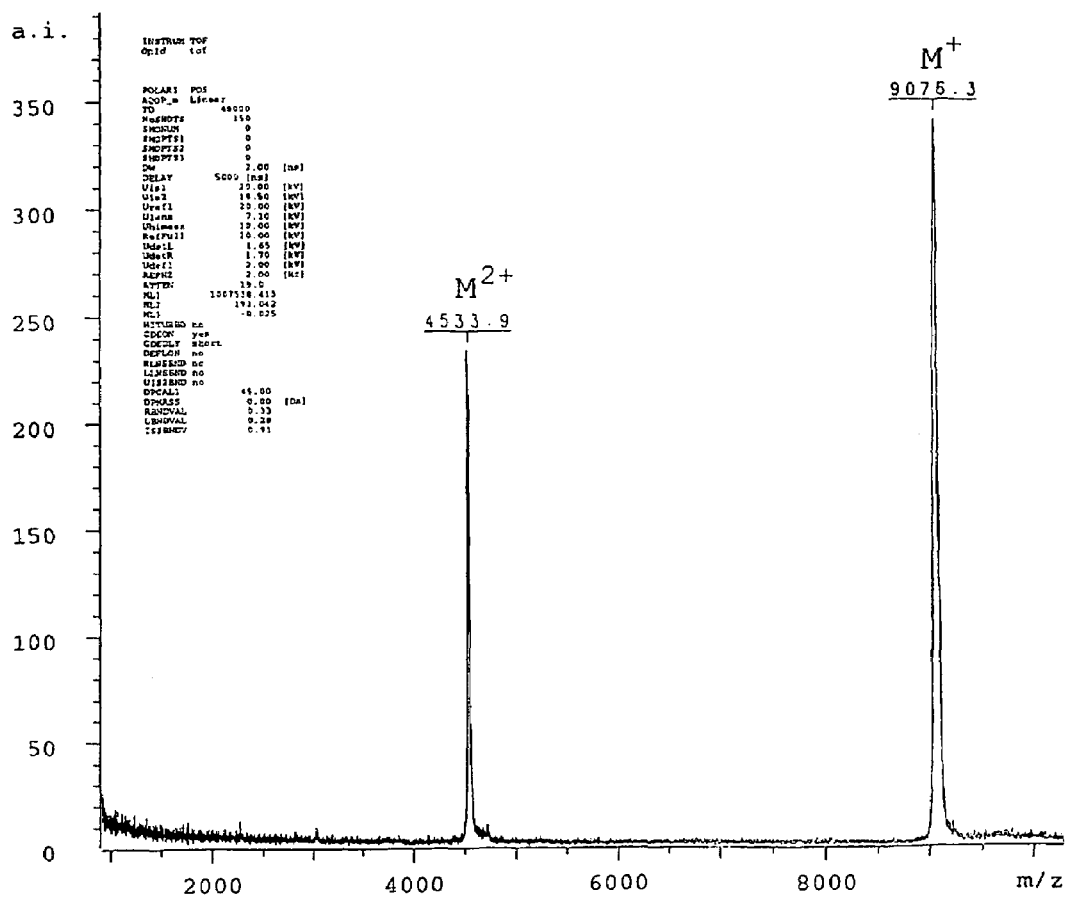
FIG. 6 depicts a MALDI mass spectrum of purified peptide FF (calcd. =9066 [M+], found=9076.3).
Figure 7:
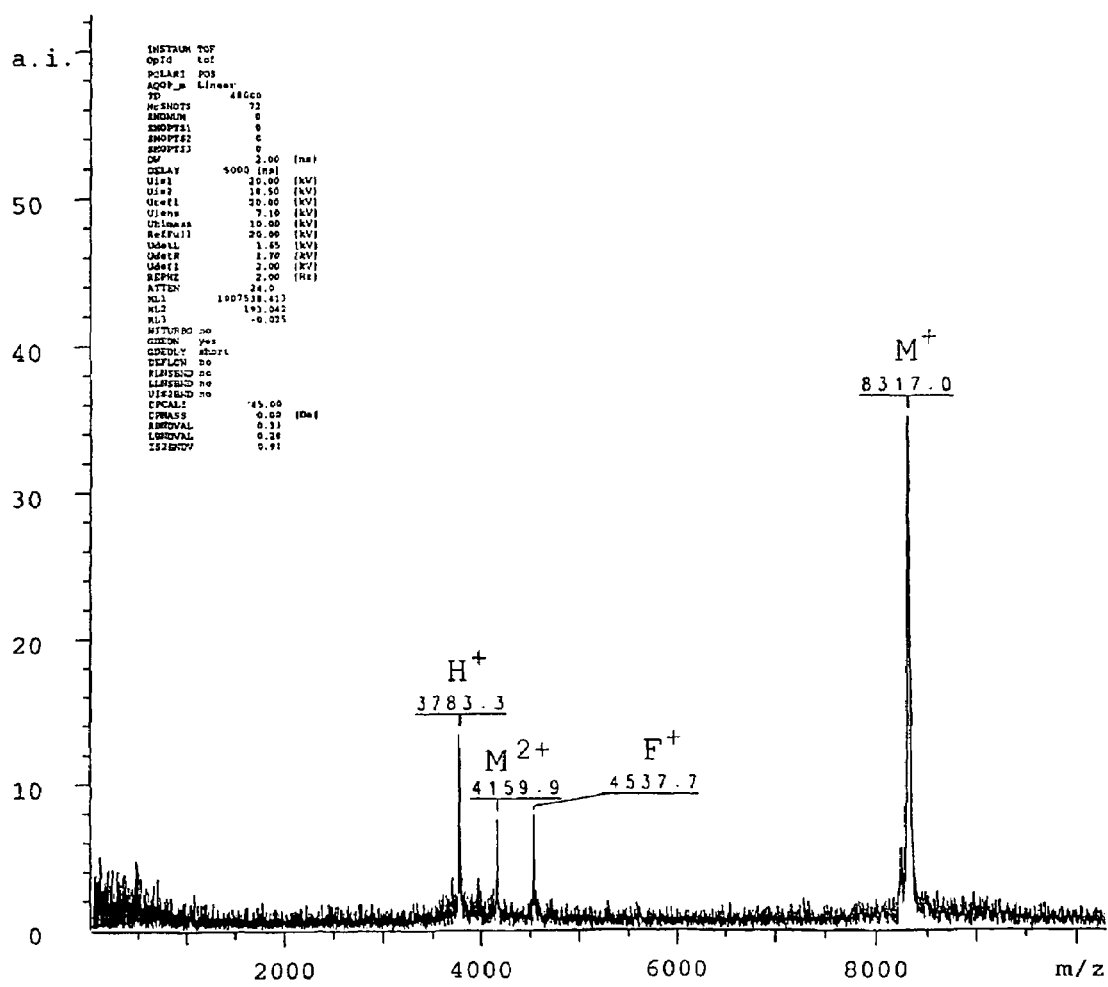
FIG. 7 depicts a MALDI mass spectrum of purified peptide HF (calcd. =8310.4 [M⁺], found=8317). The smaller peaks in the spectrum are the $M^{2+}$ peak (4159.9), and monomeric H (3783.3) and monomeric F (4537.7) peptides, resulting from the cleavage of the HF disulfide bond during the MALDI experiment.
Figure 8:
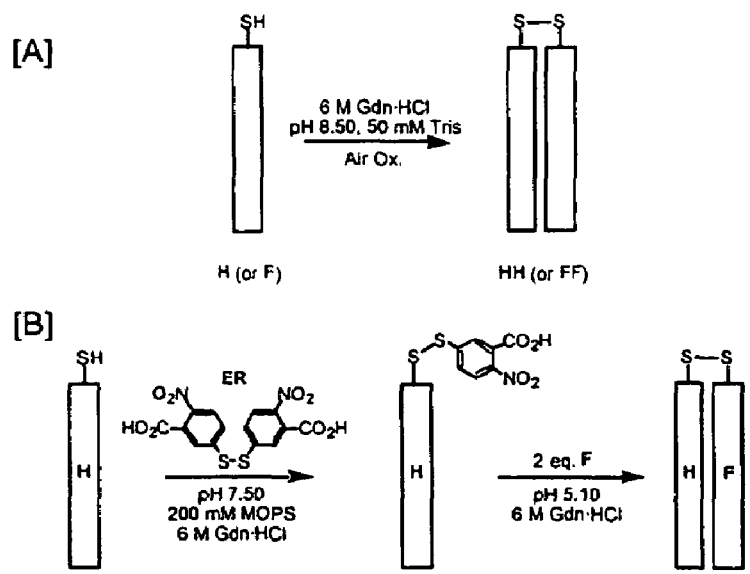
FIG. 8 depicts the synthesis of the homodimer and the heterodimer. [A] Disulfide bonded homodimers HH and FF were synthesized by air oxidation of monomeric peptides in 6 M Gdn HCl. [B] The heterodimer HF was synthesized by reaction of H with Ellman's reagent (ER), followed by reaction with excess F.
Figure 9:
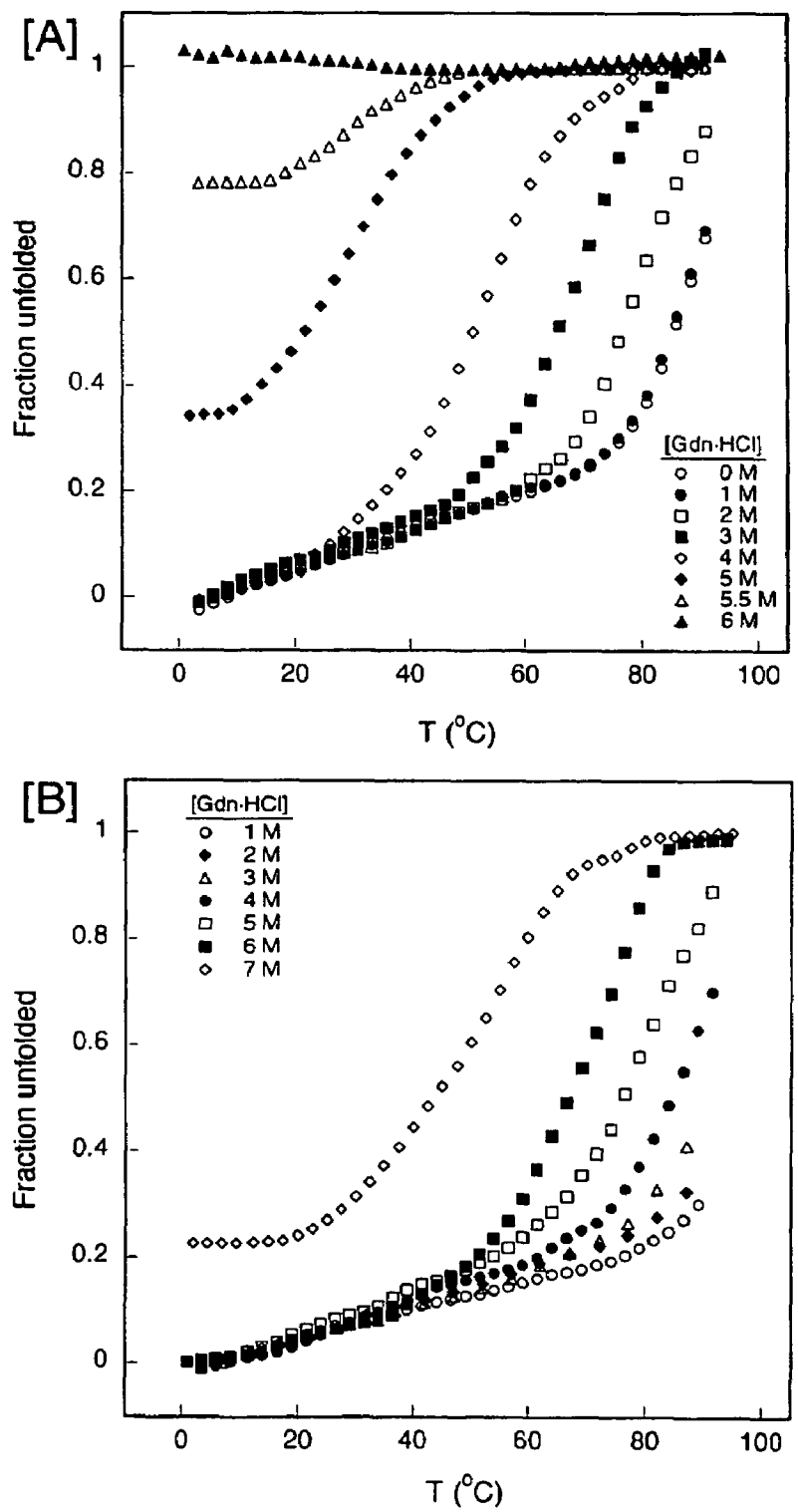
FIG. 9 depicts thermal melting curves for the two homodimers. [A] HH with increasing concentrations of guanidine hydrochloride; and [B] FF monitored by the decrease in molar ellipticity at 222 nm. Peptide concentration=2 μM
Figure 10:
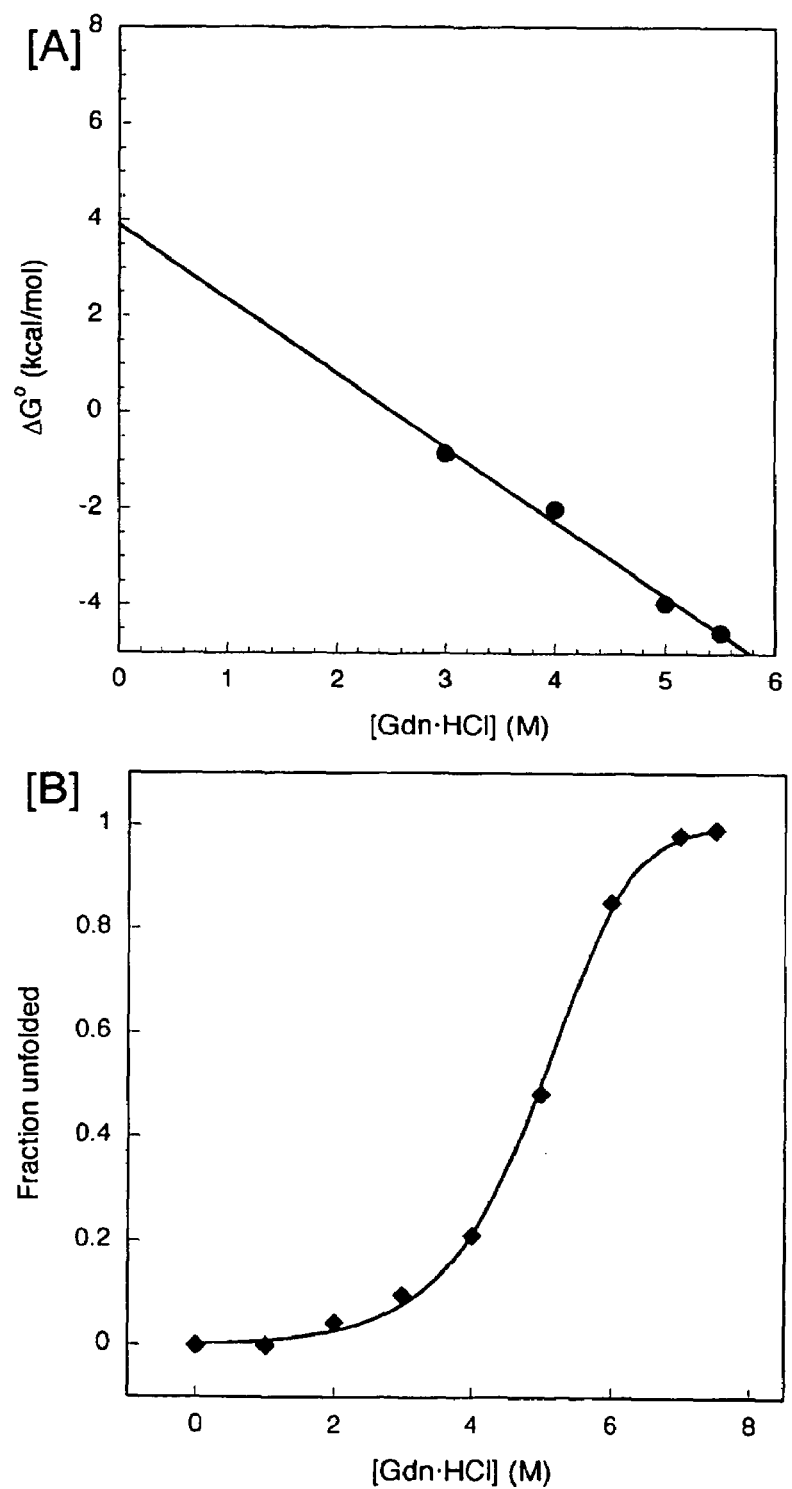
FIG. 10 depicts guanidine hydrochloride melting curves for the two heterodimers. [A] HH (at 74° C.); and [B] FF (at 80° C.). The data yield an apparent free energy of unfolding: $\Delta G_{HH}$=+3.90 kcal/mol and $\Delta G_{FF}$=+16.76 kcal/mol.
Figure 11:
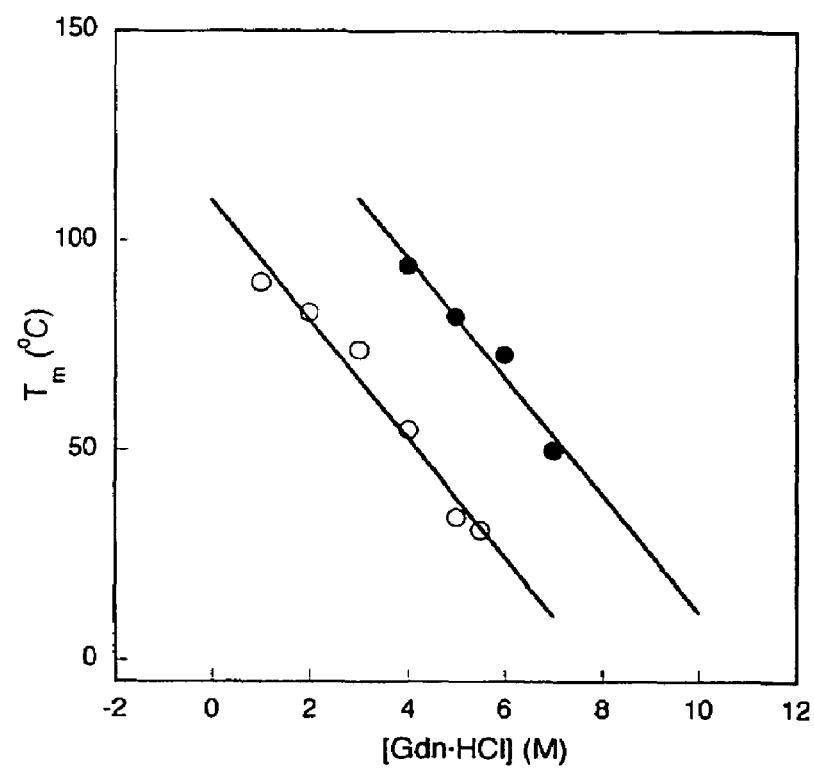
FIG. 11 presents graphically the melting temperatures ($T_m$) as a function of guanidine hydrochloride concentration for HH (○) and FF (●). At all temperatures, the fluorinated peptide is more stable.

Circular dichroism spectra of peptides HH, HF and FF revealed the alpha helical character of all three disulfide bonded dimers, showing characteristic minima at 208 and 222 nm. FIG. 3[A]. The order of stability was readily established when melting curves were monitored by CD are compared. All three peptides HF, RH and FF displayed cooperative unfolding transitions as a function of temperature in the presence of guanidine hydrochloride (Gdn HCl). The melting temperatures in 5 M Gdn HCl of HH (34° C.) and that of HF (36° C.) were similar. In contrast, the fluorinated peptide FF meltrd at an estimated 82° C. under these conditions. FIG. 3[B]. The fluorinated disulfide bonded dimer displayed remarkable stability, resisting even minimal denaturation at 6 M Gdn HCl at room temperature. Even at 7 M Gdn HCl concentration, FF resisted thermal denaturation up to 45° C. Table 1. Thus, the fluorinated assembly FF is significantly more stable than either the heterodimer HF or the hydrocarbon homodimer HH. A priori, the $T_m$ of the heterodimer can be expected to be the average of the $T_m$ values of the homodimers ($\Delta T_m = 0$). The specificity for heterodimer formation can be approximated by $\Delta T_m = T_m(\text{heterodimer HF}) - \frac{1}{2}[T_m(\text{homodimer HH}) + T_m(\text{homodimer FF})] = -22°$ C. Differences in $\Delta T_m$ have been invoked to explain the specificity of the heterodimeric Fos-Jun peptide pair. O'Shea, E. K.; Rutkowski, R.; Kim, P. S. *Cell* 1992, 68, 69–708. In our case, $\Delta T_m$ is −22° C., i.e. the thermal stability of the heterodimer is appreciably lower than the expected intermediate stability. The thermodynamic consequence of the relative stability of the fluorinated peptide assembly FF and the instability of HF is to shift the equilibrium away from the heterodimer to the homodimers.

Sedimentation equilibrium analysis of the disulfide bonded dimers in the 2–15 μM range revealed that HH has an apparent molecular weight of 7501 D in solution, consistent with two helices forming the coiled coil structure. Table 1. In contrast, FF sediments with an apparent molecular weight of 17835 D. This could be due to much larger association constant of FF monomers or due to the larger size of the core formed by hexafluoroleucine forcing it to adopt a coiled coil structure with four helices.

In sum, we have demonstrated the incorporation of hexafluoroleucine as the sole hydrophobic core residue in a designed coiled-coil. Furthermore, this is the first example of a very highly specific protein-protein interaction based on the substitution of the hydrophobic core with fluorinated residues. This aspect of the invention relates to a method to design and manipulate specific helix-helix interactions within the context of the nonpolar environment of membranes. See Choma, C.; Gratkowski, H.; Lear, J. D.; DeGrado, W. F. *Nature Struct. Biol.* 2000, 7, 161–166; and Zhou, F. X.; Cocco, M. J.; Russ, W. P.; Brunger, A. T.; Engelman, D. M. *Nature Struct. Biol.* 2000, 7, 154–160.

Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

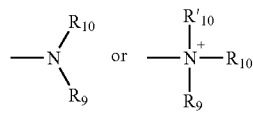

wherein R$_9$, R$_{10}$ and R'$_{10}$ each independently represent a group permitted by the rules of valence.

The term "acylamino" is art-recognized and refers to a moiety that can be represented by the general formula:

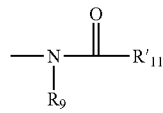

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

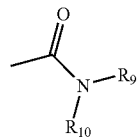

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

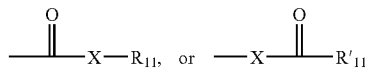

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynl, —O—(CH$_2$)$_m$—R$_8$, where m and R$_8$ are described above.

The term "sulfonate" is art recognized and includes a moiety that can be represented by the general formula:

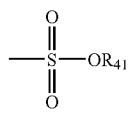

in which R$_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

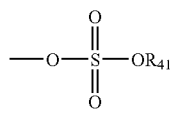

in which $R_{41}$ is as defined above.

The term "sulfonylamino" is art recognized and includes a moiety that can be represented by the general formula:

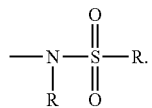

The term "sulfamoyl" is art-recognized and includes a moiety that can be represented by the general formula:

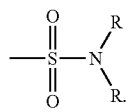

The term "sulfonyl", as used herein, refers to a moiety that can be represented by the general formula:

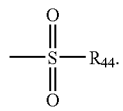

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

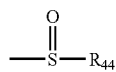

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, the present invention relates to a compound represented by A:

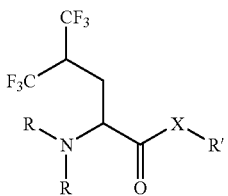

wherein

X represents O, S, N(R), or C(R)$_2$;

R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;

R' represents H, alkyl, aryl, heteroaryl, aralkyl, or heteroaralkyl; or XR' represents halide;

the stereochemical configuration at any stereocenter of a compound represented by A may be R, S, or a mixture of these configurations; and the enantiomeric excess of a compound represented by A is greater than or equal to about 85%.

In certain embodiments, the compounds of the present invention are represented by general structure A and the attendant definitions, wherein X represents O or N(R).

In certain embodiments, the compounds of the present invention are represented by general structure A and the attendant definitions, wherein R represents independently for each occurrence H, alkyl, aralkyl, acyl, alkoxycarbonyl, aralkoxycarbonyl, aralkylaminocarbonyl, or aralkylaminocarbonyl.

In certain embodiments, the compounds of the present invention are represented by general structure A and the attendant definitions, wherein R represents independently for each occurrence H.

In certain embodiments, the compounds of the present invention are represented by general structure A and the attendant definitions, wherein R' represents H, alkyl, or aralkyl.

In certain embodiments, the compounds of the present invention are represented by general structure A and the attendant definitions, wherein R' represents H.

In certain embodiments, the compounds of the present invention are represented by general structure A and the attendant definitions, wherein R represents independently for each occurrence H; and R' represents H.

In certain embodiments, the compounds of the present invention are represented by general structure A and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure A and the attendant definitions, wherein X represents O or N(R); and R represents independently for each occurrence H.

In certain embodiments, the compounds of the present invention are represented by general structure A and the attendant definitions, wherein X represents O or N(R); and R' represents H, alkyl, or aralkyl.

In certain embodiments, the compounds of the present invention are represented by general structure A and the attendant definitions, wherein X represents O or N(R); and R' represents H.

In certain embodiments, the compounds of the present invention are represented by general structure A and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, alkyl, or aralkyl.

In certain embodiments, the compounds of the present invention are represented by general structure A and the attendant definitions, wherein X represents O or N(R); R represents independently for each occurrence H; and R' represents H, alkyl, or aralkyl.

In certain embodiments, the compounds of the present invention are represented by general structure A and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure A and the attendant definitions, wherein X represents O or N(R); R represents independently for each occurrence H; and R' represents H.

In certain embodiments, the present invention relates to a compound represented by B:

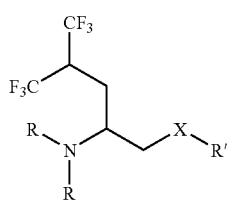

wherein

X represents O, S, N(R), or C(R)$_2$;

R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;

R' represents H, alkyl, aryl, heteroaryl, aralkyl, heteroaralkyl, formyl, acyl, alkoxycarbonyl, aralkoxycarbonyl, alkylaminocarbonyl, or aralkylaminocarbonyl; or XR' represents halide;

the stereochemical configuration at any stereocenter of a compound represented by B may be R, S, or a mixture of these configurations; and the enantiomeric excess of a compound represented by B is greater than or equal to about 85%.

In certain embodiments, the compounds of the present invention are represented by general structure B and the attendant definitions, wherein X represents O or N(R).

In certain embodiments, the compounds of the present invention are represented by general structure B and the attendant definitions, wherein R represents independently for each occurrence H, alkyl, aralkyl, acyl, alkoxycarbonyl, aralkoxycarbonyl, aralkylaminocarbonyl, or aralkylaminocarbonyl.

In certain embodiments, the compounds of the present invention are represented by general structure B and the attendant definitions, wherein R represents independently for each occurrence H.

In certain embodiments, the compounds of the present invention are represented by general structure B and the attendant definitions, wherein R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure B and the attendant definitions, wherein R' represents H.

In certain embodiments, the compounds of the present invention are represented by general structure B and the attendant definitions, wherein R represents independently for each occurrence H; and R' represents H.

In certain embodiments, the compounds of the present invention are represented by general structure B and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure B and the attendant definitions, wherein X represents O or N(R); and R represents independently for each occurrence H.

In certain embodiments, the compounds of the present invention are represented by general structure B and the attendant definitions, wherein X represents O or N(R); and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure B and the attendant definitions, wherein X represents O or N(R); and R' represents H.

In certain embodiments, the compounds of the present invention are represented by general structure B and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure B and the attendant definitions, wherein X represents O or N(R); R represents independently for each occurrence H; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure B and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure B and the attendant definitions, wherein X represents O or N(R); R represents independently for each occurrence H; and R' represents H.

In certain embodiments, the present invention relates to a compound represented by C:

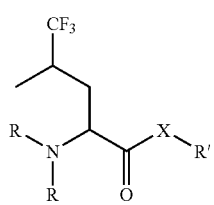

wherein
X represents O, S, N(R), or C(R)$_2$;
R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;
R' represents H, alkyl, aryl, heteroaryl, aralkyl, or heteroaralkyl; or XR' represents halide;
the stereochemical configuration at any stereocenter of a compound represented by C may be R, S, or a mixture of these configurations; and
the enantiomeric excess of a compound represented by C is greater than or equal to about 85%.

In certain embodiments, the compounds of the present invention are represented by general structure C and the attendant definitions, wherein X represents O or N(R).

In certain embodiments, the compounds of the present invention are represented by general structure C and the attendant definitions, wherein R represents independently for each occurrence H, alkyl, aralkyl, acyl, alkoxycarbonyl, aralkoxycarbonyl, aralkylaminocarbonyl, or aralkylaminocarbonyl.

In certain embodiments, the compounds of the present invention are represented by general structure C and the attendant definitions, wherein R represents independently for each occurrence H.

In certain embodiments, the compounds of the present invention are represented by general structure C and the attendant definitions, wherein R' represents H, alkyl, or aralkyl.

In certain embodiments, the compounds of the present invention are represented by general structure C and the attendant definitions, wherein R' represents H.

In certain embodiments, the compounds of the present invention are represented by general structure C and the attendant definitions, wherein R represents independently for each occurrence H; and R' represents H.

In certain embodiments, the compounds of the present invention are represented by general structure C and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure C and the attendant definitions, wherein X represents O or N(R); and R represents independently for each occurrence H.

In certain embodiments, the compounds of the present invention are represented by general structure C and the attendant definitions, wherein X represents O or N(R); and R' represents H, alkyl, or aralkyl.

In certain embodiments, the compounds of the present invention are represented by general structure C and the attendant definitions, wherein X represents O or N(R); and R' represents H.

In certain embodiments, the compounds of the present invention are represented by general structure C and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, alkyl, or aralkyl.

In certain embodiments, the compounds of the present invention are represented by general structure C and the attendant definitions, wherein X represents O or N(R); R represents independently for each occurrence H; and R' represents H, alkyl, or aralkyl.

In certain embodiments, the compounds of the present invention are represented by general structure C and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure C and the attendant definitions, wherein X represents O or N(R); R represents independently for each occurrence H; and R' represents H.

In certain embodiments, the present invention relates to a compound represented by

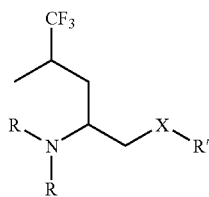

D wherein

X represents O, S, N(R), or C(R)$_2$;

R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;

R' represents H, alkyl, aryl, heteroaryl, aralkyl, heteroaralkyl, formyl, acyl, alkoxycarbonyl, aralkoxycarbonyl, alkylaminocarbonyl, or aralkylaminocarbonyl; or XR' represents halide;

the stereochemical configuration at any stereocenter of a compound represented by D may be R, S, or a mixture of these configurations; and the enantiomeric excess of a compound represented by D is greater than or equal to about 85%.

In certain embodiments, the compounds of the present invention are represented by general structure D and the attendant definitions, wherein X represents O or N(R).

In certain embodiments, the compounds of the present invention are represented by general structure D and the attendant definitions, wherein R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein R' represents independently for each occurrence H.

In certain embodiments, the compounds of the present invention are represented by general structure D and the attendant definitions, wherein R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein R' represents H.

In certain embodiments, the compounds of the present invention are represented by general structure D and the attendant definitions, wherein R represents independently for each occurrence H; and R' represents H.

In certain embodiments, the compounds of the present invention are represented by general structure D and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein X represents O or N(R); and R represents independently for each occurrence H.

In certain embodiments, the compounds of the present invention are represented by general structure D and the attendant definitions, wherein X represents O or N(R); and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein X represents O or N(R); and R' represents H.

In certain embodiments, the compounds of the present invention are represented by general structure D and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein X represents O or N(R); R represents independently for each occurrence H; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure D and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure D and the attendant definitions, wherein X represents O or N(R); R represents independently for each occurrence H; and R' represents H.

In certain embodiments, the present invention relates to a compound represented by E:

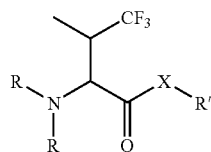

E wherein

X represents O, S, N(R), or C(R)$_2$;

R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;

R' represents H, alkyl, aryl, heteroaryl, aralkyl, or heteroaralkyl; or XR' represents halide;

the stereochemical configuration at any stereocenter of a compound represented by E may be R, S, or a mixture of these configurations; and the enantiomeric excess of a compound represented by E is greater than or equal to about 85%.

In certain embodiments, the compounds of the present invention are represented by general structure E and the attendant definitions, wherein X represents O or N(R).

In certain embodiments, the compounds of the present invention are represented by general structure E and the attendant definitions, wherein R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure E and the attendant definitions, wherein R represents independently for each occurrence H.

In certain embodiments, the compounds of the present invention are represented by general structure E and the attendant definitions, wherein R' represents H, alkyl, or aralkyl.

In certain embodiments, the compounds of the present invention are represented by general structure E and the attendant definitions, wherein R' represents H.

In certain embodiments, the compounds of the present invention are represented by general structure E and the attendant definitions, wherein R represents independently for each occurrence H; and R' represents H.

In certain embodiments, the compounds of the present invention are represented by general structure E and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure E and the attendant definitions, wherein X represents O or N(R); and R represents independently for each occurrence H.

In certain embodiments, the compounds of the present invention are represented by general structure E and the attendant definitions, wherein X represents O or N(R); and R' represents H, alkyl, or aralkyl.

In certain embodiments, the compounds of the present invention are represented by general structure E and the attendant definitions, wherein X represents O or N(R); and R' represents H.

In certain embodiments, the compounds of the present invention are represented by general structure E and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, alkyl, or aralkyl.

In certain embodiments, the compounds of the present invention are represented by general structure E and the attendant definitions, wherein X represents O or N(R); R represents independently for each occurrence H; and R' represents H, alkyl, or aralkyl.

In certain embodiments, the compounds of the present invention are represented by general structure E and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure E and the attendant definitions, wherein X represents O or N(R); R represents independently for each occurrence H; and R' represents H.

In certain embodiments, the present invention relates to a compound represented by F:

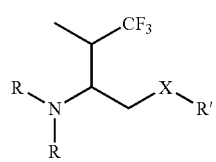

F wherein

X represents O, S, N(R), or C(R)$_2$;

R represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;

R' represents H, alkyl, aryl, heteroaryl, aralkyl, heteroaralkyl, formyl, acyl, alkoxycarbonyl, aralkoxycarbonyl, alkylaminocarbonyl, or aralkylaminocarbonyl; or XR' represents halide;

the stereochemical configuration at any stereocenter of a compound represented by F may be R, S, or a mixture of these configurations; and the enantiomeric excess of a compound represented by F is greater than or equal to about 85%.

In certain embodiments, the compounds of the present invention are represented by general structure F and the attendant definitions, wherein X represents O or N(R).

In certain embodiments, the compounds of the present invention are represented by general structure F and the attendant definitions, wherein R represents independently for each occurrence H, alkyl, aralkyl, acyl, alkoxycarbonyl, aralkoxycarbonyl, aralkylaminocarbonyl, or aralkylaminocarbonyl.

In certain embodiments, the compounds of the present invention are represented by general structure F and the attendant definitions, wherein R represents independently for each occurrence H.

In certain embodiments, the compounds of the present invention are represented by general structure F and the attendant definitions, wherein R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure F and the attendant definitions, wherein R' represents H.

In certain embodiments, the compounds of the present invention are represented by general structure F and the attendant definitions, wherein R represents independently for each occurrence H; and R' represents H.

In certain embodiments, the compounds of the present invention are represented by general structure F and the attendant definitions, wherein X represents O or N(R); and R represents independently for each occurrence H, alkyl, aralkyl, acyl, alkoxycarbonyl, aralkoxycarbonyl, alkylaminocarbonyl, or aralkylaminocarbonyl.

In certain embodiments, the compounds of the present invention are represented by general structure F and the attendant definitions, wherein X represents O or N(R); and R represents independently for each occurrence H.

In certain embodiments, the compounds of the present invention are represented by general structure F and the attendant definitions, wherein X represents O or N(R); and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure F and the attendant definitions, wherein X represents O or N(R); and R' represents H.

In certain embodiments, the compounds of the present invention are represented by general structure F and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure F and the attendant definitions, wherein X represents O or N(R); R represents independently for each occurrence H; and R' represents H, aralkyl, formyl, acyl, alkoxycarbonyl, aralkoxycarbonyl, alkylaminocarbonyl, or aralkylaminocarbonyl.

In certain embodiments, the compounds of the present invention are represented by general structure F and the attendant definitions, wherein X represents O or N(R); R represents independently for each occurrence H, alkyl, aralkyl, acyl, alkoxycarbonyl, aralkoxycarbonyl, alkylaminocarbonyl, or aralkylaminocarbonyl; and R' represents H.

In certain embodiments, the compounds of the present invention are represented by general structure F and the attendant definitions, wherein X represents O or N(R); R represents independently for each occurrence H; and R' represents H.

In certain embodiments, the present invention relates to a compound represented by any of the structures outlined above, wherein the enantiomeric excess of said compound is greater than or equal to about 90%.

In certain embodiments, the present invention relates to a compound represented by any of the structures outlined above, wherein the enantiomeric excess of said compound is greater than or equal to about 95%.

In certain embodiments, the present invention relates to a compound represented by any of the structures outlined above, wherein said compound is a single stereoisomer.

In certain embodiments, the present invention relates to a compound represented by any of the structures outlined above, wherein said compound is in the form of a salt.

In certain embodiments, the present invention relates to a formulation, comprising a compound represented by any of the structures outlined above; and a pharmaceutically acceptable excipient.

In certain embodiments, the present invention relates to an oligopeptide or a polypeptide, comprising a compound represented by any of the structures outlined above.

Methods of the Invention

In certain embodiments, the present invention relates to a method of resolving into individual enantiomers a mixture of diastereomers of a compound represented by structure A, B, C, D, E, or F, comprising the steps of:

(a) using chromatography to obtain an individual pair of enantiomers of a compound represented by structure A, B, C, D, E, or F from a mixture of diastereomers of said compound; and (b) using enzymatic hydrolysis to obtain a single enantiomer of said compound from the individual pair of enantiomers of said compound.

In certain embodiments, the present invention relates to the aforementioned resolution method, wherein $(R)_2N$ represents (alkoxycarbonyl)HN in the mixture of diastereomers.

In certain embodiments, the present invention relates to the aforementioned resolution method, wherein $(R)_2N$ represents (tert-butyloxycarbonyl)HN in the mixture of diastereomers.

In certain embodiments, the present invention relates to the aforementioned resolution method, wherein $(R)_2N$ represents (acyl)HN in the the individual pair of enantiomers subjected to enzymatic hydrolysis.

In certain embodiments, the present invention relates to the aforementioned resolution method, wherein $(R)_2N$ represents (acetyl)HN in the the individual pair of enantiomers subjected to enzymatic hydrolysis.

In certain embodiments, the present invention relates to the aforementioned resolution method, wherein the enzyme used is porcine kidney acylase I.

In certain embodiments, the present invention relates to the aforementioned resolution method, wherein $(R)_2N$ represents (alkoxycarbonyl)HN in the mixture of diastereomers; and $(R)_2N$ represents (acyl)HN in the the individual pair of enantiomers subjected to enzymatic hydrolysis.

In certain embodiments, the present invention relates to the aforementioned resolution method, wherein $(R)_2N$ represents (tert-butyloxycarbonyl)HN in the mixture of diastereomers; and $(R)_2N$ represents (acetyl)HN in the the individual pair of enantiomers subjected to enzymatic hydrolysis.

In certain embodiments, the present invention relates to the aforementioned resolution method, wherein $(R)_2N$ represents (alkoxycarbonyl)HN in the mixture of diastereomers; $(R)_2N$ represents (acyl)HN in the the individual pair of enantiomers subjected to enzymatic hydrolysis; and the enzyme used is porcine kidney acylase I.

In certain embodiments, the present invention relates to the aforementioned resolution method, wherein $(R)_2N$ represents (tert-butyloxycarbonyl)HN in the mixture of diastereomers; $(R)_2N$ represents (acetyl)HN in the the individual pair of enantiomers subjected to enzymatic hydrolysis; and the enzyme used is porcine kidney acylase I.

In certain embodiments, the present invention relates to a method of synthesizing a non-native oligopeptide, polypeptide or protein with enhanced hydrophobicity relative to a native oligopeptide, polypeptide or protein, comprising the step of using a compound represented by structure A, B, C, D, E, or F in place of a leucine or valine in a synthesis of an oligopeptide, polypeptide or protein.

In certain embodiments, the present invention relates to the aforementioned method of synthesizing a non-native oligopeptide, polypeptide or protein with enhanced hydrophobicity, wherein the synthesis is automated.

In certain embodiments, the present invention relates to a method of enhancing the hydrophobicity of an oligopeptide, polypeptide or protein, comprising the step of replacing a leucine or valine in an oligopeptide, polypeptide or protein with a compound represented by structure A, B, C, D, E, or F.

In certain embodiments, the present invention relates to a method of synthesizing a trifluoromethyl-containing analogue of norvaline or valine, comprising the steps of:

(a) oxidizing a protected serine or homoserine to give an aldehyde;

(b) reacting the aldehyde with trimethyl(trifluoromethyl) silane and fluoride to give a secondary alcohol;

(c) acylating the secondary alcohol using an aryl chlorothionoformate to give a thionocarbonate; and (d) reducing the thionocarbonate using a tin hydride and an initiator to give a trifluoromethyl-containing analogue of norvaline or valine.

In certain embodiments, the present invention relates to a method of synthesizing a trifluoromethyl-containing analogue of leucine, comprising the steps of:

(a) oxidizing a protected homoserine to give an aldehyde;

(b) reacting the aldehyde with trimethyl(trifluoromethyl) silane and fluoride to give a secondary alcohol;

(c) oxidizing the secondary alcohol to give a trifluoromethyl ketone;

(d) reacting the trifluoromethyl ketone with (methylene) triphenylphosphine to give an alkene; and (e) hydrogenating the alkene to give a trifluoromethyl-containing analogue of leucine.

In certain embodiments, the present invention relates to a method of synthesizing protected 5,5,5,5',5',5'-hexafluoroleucine, comprising the steps of:

(a) reacting an oxazolidine aldehyde derived from serine with a hexafluoroisopropylidene ylide to give an oxazolidine 1,1-bis(trifluoromethyl)alkene;

(b) hydrogenating the oxazolidine 1,1-bis(trifluoromethyl)alkene to give an oxazolidine 1,1-bis(trifluoromethyl) alkane;

(c) hydrolyzing the oxazolidine 1,1-bis(trifluoromethyl) alkane to give a protected amino alcohol; and (d) oxidizing the protected amino alcohol to give protected 5,5,5,5',5',5'-hexafluoroleucine.

In certain embodiments, the present invention relates to the aforemetioned method of synthesizing protected 5,5,5, 5',5',5'-hexafluoroleucine, wherein the reagents for step (a) comprise triphenylphosphine and $[(CF_3)_2C]_2S_2$; the reagents for step (b) comprise hydrogen and 10% palladium on carbon; the reagents for step (c) comprise toluenesulfonic acid and methanol; and the reagents for step (d) comprise pyridinium dichromate.

In certain embodiments, the present invention relates to a method of preparing a compound represented by 6, comprising the steps depicted in Scheme 1:

Scheme 1.

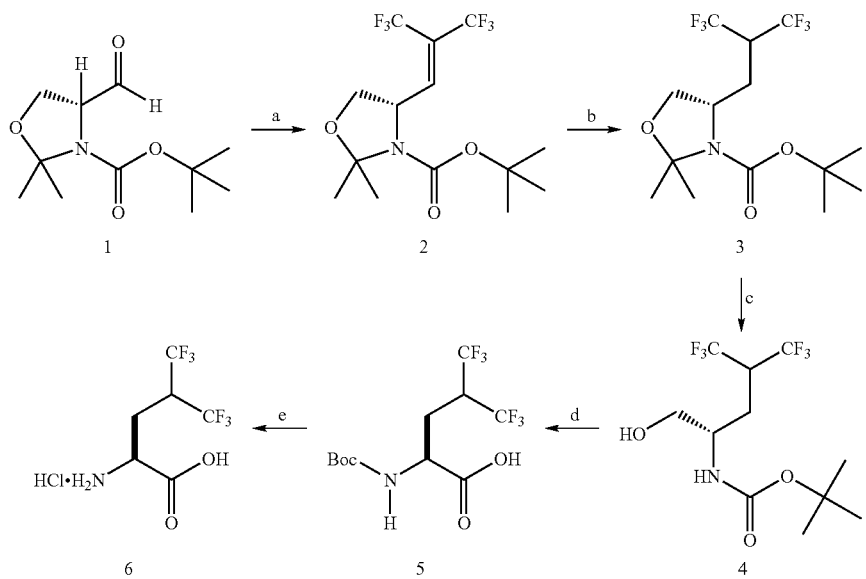

Reagents and condition: (a) PPh₃, [(CF₃)₂C]₂S₂, Et₂O, -78° C. → rt, 3 d, 92%; (b) H₂, 10% Pd/C, THF, 98%; (c) TsOH, MeOH, rt, 1 d, 80%; (d) PDC, DMF, 18 hrs., 75% (e) 40% CF₃CO₂H/CH₂Cl₂; HCl wash, 10 min., rt, >95%.

Exemplification

The invention now being generally described, it will be more readily understood by reference to the following examples, which are included merely for purposes of illustration of certain aspects and embodiments of the present invention, and are not intended to limit the invention.

EXAMPLE 1

General Experimental Procedures

Melting points were determined in open capillaries on a MEL-TEMP II apparatus (Laboratory Devices, Inc., Holliston, Mass.) and are uncorrected. All reactions requiring non-aqueous conditions were performed in oven-dried glassware under positive pressure of argon. Flash column chromatography was performed by forced flow of solvent using Kieselgel 60 SiO₂ (230–240 mesh) gel (EM Science) packed into glass columns using standard litertaure procedures. Still, W. C.; Kahn, M.; Mitra, A. *J. Org. Chem.* 1978, 43, 2923. Analytical thin layer chromatography was performed using E. Merck silica gel Kieselgel 60 F₂₅₄ (0.25 mm) plates. Compounds were visualized by UV light, exposure to iodine vapour or by staining with a ninhydrin solution followed by heating. Reagents and solvents were of reagent grade or better and were obtained from Aldrich Chemical Co., Fluka Chemie AG, Lancaster Synthesis or Novabiochem Corp. Deuterated solvents were obtained from Cambridge Isotope Laboratories.

Infra-red spectra were obtained on a Mattson 1000 FT-IR instrument with a 4 cm⁻1 bandpass. Spectra of solid samples were obtained as solid thin-films or dissolved in thin layers of organic solvents between NaCl plates. Mass Spectra were obtained on a Hewlett Packard GC-MS (Model 5988A) with a dip-probe using conditions as indicated. Nuclear magnetic resonance spectra were recorded on a Bruker AM-300 or a Bruker DPX-300 instrument in standard deuterated solvents. Optical rotations were measured using an AUTOPOL IV digital polarimeter (Rudolph Research Analytical, N.J.).

EXAMPLE 2

Synthesis of Bis-trifluoromethyl Olefin (2)

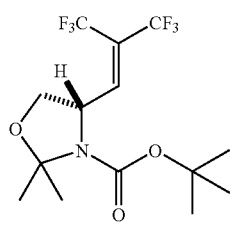

2

Typical procedure for the coupling reaction: To a stirred solution of the Garner aldehyde 1 (7.0 g, 31.0 mmol) and PPh₃ (57 g, 217 mmol) in dry Et₂O (300 mL) was added 2,2,4,4-tetrakis-(trifluoromethyl)-1,3-dithietane (39.5 g, 108.5 mmol) at −78° C. under argon. The mixture was stirred for 3 d while being slowly warmed to room temperature. The reaction slowly accumulated an insoluble white solid which was filtered and the filtrate concentrated. The residue was further dissolved in n-pentane (300 mL) and filtered again to remove insoluble impurities. After removal of the solvent, the residue was subjected to flash column chromatography using n-pentane/Et₂O (6/1) as eluant to give pure 2 as a pale yellow oil (10.4 g, 92%). ¹H NMR (300 MHz, CDCl₃) δ 6.70 (d, 1H, J=8.7 Hz), 4.81 (bs, 1H), 4.23 (dd, 1H, J=6.9 Hz, 9.3 Hz), 3.79 (dd, 1H, J=3.9 Hz, 9.3 Hz), 1.65 (s, 3H), 1.56 (s, 3H), 1.42 (s, 9H); $^{19}$F NMR (282.6 MHz, CDCl$_3$/CFCl$_3$) δ −65.01 (d, 3F, J=5.9 Hz), −58.44 (d, 3F, J=5.9 Hz); FT-IR (film, V$_{max}$, cm$^{-1}$) 2983m, 2935m, 2885w, 1713s, 1479W, 1460w, 1379s, 1230s, 1165s, 1110m, 971m; [α]$_D^{26.1}$=+12.3° (c 1.7, CHCl$_3$); GC-MS (CI, CH$_4$): 364 (1, [M+1]$^+$), 336 (18), 308 (100), 288 (98), 264 (37), 102 (2), 57 (9).

EXAMPLE 3

Synthesis of Oxazolidine (3)

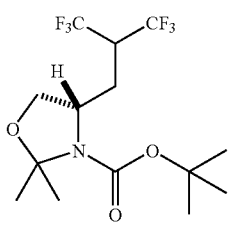

3

A 500 mL round bottomed flask was charged with a solution of 2 (10.3 g, 28.3 mmol) in THF (250 mL) and 10% Pd/C (40 g). The reaction flask was purged with argon and hydrogen sequentially and stirred under hydrogen at room temperature until uptake of H$_2$ ceased (24 hours). The catalyst was then separated from the reaction mixture by filtration (and can be used again). The filtrate was dried over anhydrous MgSO$_4$ and concentrated by rotary evaporation to give 3 (10.1 g, 98% yield) as a pale yellow oil. $^1$H NMR (300 MHz, CDCl$_3$) δ 4.23 (4.05) (m, 1H), 4.00 (dd, 1H, J=5.4 Hz, 9.3 Hz), 3.73 (d, 1H, J=9.3 Hz), 3.58 (3.05) (m, 1H), 2.18 (2.01) (m, 2H), 1.62 (1.58) (s, 3H), 1.48 (br. s, 12H); $^{13}$C NMR (75.5 MHz, CDCl$_3$) δ 153.22 (151.51) (C=O), 123.89 (q, 2×CF$_3$, $^1J_{CF}$=284.0), 94.47 (94.03) (C), 80.85 (80.73) (C), 67.26 (66.65) (CH$_2$), 55.58 (55.12) (CH), 45.44 (45.12) (quintet, CH, $^2J_{CF}$=27.2 Hz), 28.98 (28.00) (CH$_2$), 28.25 (3×CH$_3$), 27,58 (26.90) (CH$_3$), 24.15 (22.86) (CH$_3$); $^{19}$F NMR (282.6 MHz, CDCl$_3$/CFCl$_3$) δ−67.68−−68.42 (m); FT-IR (film, v$_{max}$, cm$^{-1}$): 2984m, 2941m, 2884w, 1704s, 1457m, 1393s, 1258s, 1168s, 1104s, 847m; [α]$_D^{22.4}$=+17.5° (c 0.4, CHCl$_3$); GC-MS (CI, CH$_4$): 366 (4, [M+1]$^+$), 338 (16), 310 (100), 290 (48), 266 (48), 57 (8).

EXAMPLE 4

Synthesis of N-Boc-5,5,5,5',5',5'-(S)-Hexafluoroleucinol (4)

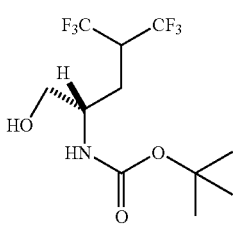

4

To a solution of 3 (10.1 g, 27.6 mmol) in CH$_2$Cl$_2$ (30 mL) was added 10 mL of trifluoroacetic acid (TFA). The reaction mixture was stirred at room temperature for 5 min. After removal of the solvent and TFA, the residue was partitioned between 150 mL of ethyl ether and 100 mL of H$_2$O. The organic layer was washed with water (20 mL×4), dried over MgSO$_4$, and concentrated to give 4 (7.2 g, 80% yield) as a white solid. The aqueous layers contain a completely deprotected product due to cleavage of the BOC moiety as evidenced by ninhydrin active material. This hexafluoroamino alcohol can be converted back to 4 by protecting the free amine group as a BOC amide. $^1$H NMR (300 MHz, CDCl$_3$) δ 5.03 (d, 1H, J=8.1 Hz), 3.84 (m, 1H), 3.70 (m, 2H), 3.20 (m, 1H), 3.10 (br.s, 1H), 1.98 (m, 2H), 1.45 (s, 9H); $^{13}$C NMR (75.5 MHz, CDCl$_3$) δ 156.57 (C=O), 124.00 (q, 2×CF$_3$, $^1J_{CF}$=284.0 Hz), 80.58 (C), 66.08 (CH$_2$), 50.57 (CH), 45.09 (m, CH, $^2J_{CF}$=28.1 Hz), 28.38 (3×CH$_3$), 26.44 (CH$_2$); $^{19}$F NMR (282.6 MHz, CDCl$_3$/CFCl$_3$) δ −67.96 (m), −68.46 (m); FT-IR (KBr pellet, v$_{max}$, cm$^{-1}$) 3397s (br), 3253s, 3068m, 2981s, 2948m, 1686s, 1552s, 1369s, 1289s, 1174s, 1145s, 1055s; [α]$_D^{22.9}$=−14.4° (c 1.0, CH$_3$OH); GC-MS (CI, CH$_4$); 326 (8, [M+1]$^+$), 298 (14), 270 (100), 226 (20), 57 (2); m.p.=114–115° C.

EXAMPLE 5

Synthesis of N-Boc-5,5,5,5',5',5'-(S)-Hexafluoroleucine (5)

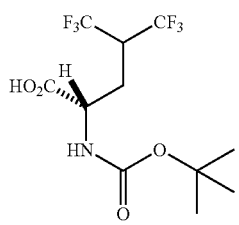

5

A mixture of 4 (7.1 g, 21.8 mmol) and pyridinium dichromate (33 g, 88 mmol) in DMF (150 mL) was stirred under argon at room temperature for 24 hrs. before 150 mL of H$_2$O was added. The mixture was then extracted with ethyl ether (400 mL×2). The combined ether layers were washed with 1 N HCl (80 mL×2) and concentrated until about 150 mL of solution left. This solution was washed with 5% NaHCO$_3$ (150 mL×3). The combined aqueous layers were acidified to pH 2 with 3 N HCl, extracted with ether again (400 mL×2). The ether layers were then dried over MgSO$_4$ and concentrated to give 5 (5.2 g, 70%) as a white solid. $^1$H NMR (300 MHz, CDCl$_3$) δ 7.36 (5.21) (d, 1H, J=6.3 Hz), 4.41 (m, 1H), 3.37 (m, 1H), 2.43–2.11 (br. m, 2H), 1.47 (s, 9H); $^{19}$F NMR (282.6 MHz, CDCl$_3$/CFCl$_3$) δ −67.87−−68.23 (m); FT-IR (KBr pellet, v$_{max}$, cm$^{-1}$) 3358–2500m (br.), 3245s, 3107m, 2989s, 2980m, 1725s, 1712s, 1657s, 1477s, 1458s, 1404s, 1296s, 1277s, 1258s, 916m; [α]$_D^{21.8}$=−23.0° (c 1.0, CH$_3$OH); GC-MS (CI, CH$_4$): 340 (21, [M+1]$^+$), 312 (7), 284 (100), 264 (16), 240 (19), 57 (39); m.p.=85–91° C.

EXAMPLE 6

Synthesis of 5,5,5,5',5',5'-(S)-Hexafluoroleucine (6)

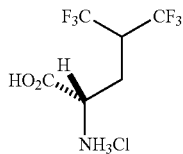

A solution of 5 (581 mg, 1.7 mmol) in 5 mL of TFA/CH$_2$Cl$_2$ (2/3) was stirred for 30 min. After removal of the solvents, the residue was partitioned between 1 N HCl (10 mL×3) and ethyl ether (10 mL). The combined aqueous layers were freeze dried to give 6 (446 mg, 95% yield) as a white solid.

EXAMPLE 7

Synthesis of Dipeptide (8)

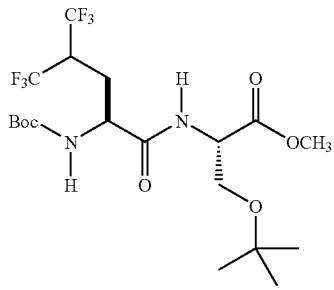

To a stirred solution of 5 (11 mg, 0.03 mmol) in anhydrous DMF (1 mL) was added diisopropyl ethyl amine (13 mg, 0.1 mmol), HBTU (13 mg, 0.03 mmol), and H-Ser(t-Bu)-OMe HCl (14 mg, 0.065 mmol) sequentially. The mixture was stirred at room temperature for 40 min before 6 mL of H$_2$O was added. The reaction mixture was extracted with ether (15 ml) and the organic layer was futher washed with 1 N HCl (5 mL×2) and 5% NaHCO$_3$ solution (5 ml), dried over MgSO$_4$, and concentrated to afford 8 (13 mg, 87% yield) as a white solid. $^1$H NMR (300 MHz, CDCl$_3$) δ 6.68 (d, 1H, J=8.1 Hz), 5.21 (d, 1H, J=8.1 Hz), 4.64 (m, 1H), 4.40 (m, 1H), 3.86 (dd, 1H, J=2.7 Hz, 9.3 Hz), 3.76 (s, 3H), 3.56 (dd, 1H, J=3.3 Hz, 9.3 Hz), 3.50 (m, 1H), 2.33–2.10 (br. m, 2H), 1.45 (s, 9H), 1.14 (s, 9H).

EXAMPLE 8

Incorporation of 5,5,5,5',5',5'-hexafluoroleucine into Peptides

The incorporation of hexafluoroleucine in a 30-residue peptide with the sequence given below has been achieved. Leucines in bold are 5,5,5,5',5',5'-(S)-hexafluoroleucine.

Peptide 1: Ac-NH-AQLKKELQALKKENAQLK-WELQALKKELAQ-CONH$_2$ The MALDI-MS of purified peptide 1 (Calc. 4316.8, found 4317.1) confirms the purity and identity of the peptide. Circular dichroism data indicates that the peptide can readily adopt an alpha helical secondary structure (characterisitic minima at 208 and 222 nm). Further biophysical studies with these peptides are in progress.

Peptide Synthesis

Peptides were prepared using the N-tert-butyloxycarbonyl (t-Boc) amino acid derivatives for Merrifield manual solid-phase synthesis (MBHA resin) using the in-situ neutralization/HBTU protocol on a 0.2 mmol scale. Schnolzer, M.; Alewood, P.; Jones, A.; Alewood.; D, Kent, S. B. *Int. J. Pept. Protein Res.* 1992, 40, 180–193. N-α-Boc-α-S-amino acids were used with the following side chain protecting groups: Arg(Tos), Asp(OBzl), Asn(Xan), Gln(Xan), Glu(OBzl) and Lys(2-Cl-Z). Peptide coupling reactions were carried out with 4-fold excess (0.8 mmol) of activated amino acid for at least 15 min. Peptides were cleaved from the resin using high HF conditions (90% anhydrous HF/10% anisole at 0° C. for 1.5 hours) with simultaneous removal of the side chain protecting groups. Tam J. P.; Merrifield, R. B. In The Peptides; Udenfriend, S., Meienhofer, J. Eds.; Academic Press Inc.: New York, 1987; Vol. 9, p 185.

In the case of hexafluoroleucine, the coupling time was extended to 2 hrs. The extent of reaction was verified by a Kaiser test after each coupling. The N-terminal was acetylated by treatment with 1:4 acetic anhydride/DMF and 6 eq. of diisopropylethylamine. The formyl protecting group on the tryptophan residue was removed by treating the resin with 1:10 piperidine in DMF solution. Peptides were cleaved from the resin by using high HF conditions (90% anhydrous HF/10% anisole at 0° C. for 1.5 h). Crude peptides were extracted with 25% acetic acid and lyophilized. Freeze dried material was dissolved in 0.1% TFA, desalted and purified by reversed phase HPLC [Vydac C4 column with a 30 min linear gradient of acetonitrile/H$_2$O/0.1% TFA at 8.0 mL/min].

HH: An aqueous solution of H (10 mg, 2.64 μmol) in 50 mM Tris (pH 8.50) and 6 M Gdn HCl (total volume: 0.75 mL) was stirred overnight at room temperature. The reaction was quenched by addition of 250 μL glacial acetic acid and diluted with 1 mL water. The mixture was directly purified by reversed phase HPLC. The fractions containing HH were collected and lyophilized to deliver 9.0 mg (90%) of HH. MALDI-MS: MW$_{calcd}$=7556.8, found: 7561.

FF: An aqueous solution of F (14 mg, 3.09 μmol) in 50 mM Tris (pH 8.50) and 6.5 M Gdn HCl (total volume: 1 mL) was stirred overnight at room temperature. The reaction was quenched by addition of 300 μL glacial acetic acid and diluted with 1.5 mL water. The mixture was directly purified by reversed phase HPLC. The fractions containing FF were pooled and lyophilized to deliver 12.1 mg (86%) of FF. MALDI-MS: MW$_{calcd}$=9066, found: 9076.3.

HF: To an aqueous solution of H (8 mg, 2.11 μmol) in MOPS buffer (pH 7.50) was added 5,5'-dithiobis(2-nitrobenzoic acid) (20 mg, 50.4 μmol). The reaction was stirred for 15 minutes and then quenched by the addition of 300 μL of neat TFA. The reaction mixture was then extracted with Et$_2$O (4×10 mL). The aqueous layer was then directly injected into a reversed-phase C18 column and purified. The fractions containing the mixed disulfide of the Ellman's reagent and H were combined and lyophilized to obtain 8.4 mg of the desired product (95%). The mixed disulfide (8 mg, 1.92 μmol) was dissolved in a pH 1.50 solution containing F (17.4 mg, 3.84 μmol). The pH was carefully adjusted to 5.10 by sequential addition of 0.1 N NaOH solution. The reaction was allowed to proceed for 20 minutes and then quenched by addition of 300 μL TFA. The reaction mixture was then directly purified by reversed phase HPLC to obtain 10 mg of pure HF (62.6%). Nearly 25% of the starting mixed disulfide was recovered unreacted. MALDI-MS: $MW_{calcd}$: 8310.4, found: 8317.

Purification

Peptides were desalted and purified by reversed phase HPLC [Vydac $C_4$ column using a 30 min linear gradient of 34–47% acetonitrile/$H_2O$/0.1% TFA at 8.0 mL/min]. Peptide 1 eluted at ~43.2% acetonitrile/$H_2O$/0.1% TFA (~30.0 min. elution time).

EXAMPLE 9

Circular Dichroism

Circular dichroism spectra were obtained on a JASCO J-715 spectropolarimeter fitted with a PTC-423S single position Peltier temperature controller. Buffer conditions were usually 10 mM phosphate (pH 7.40), 137 mM NaCl, 2.7 mM KCl unless otherwise noted. The spectrometer was calibrated with an aqueous solution of recrystallized $d_{10}$-(+)-camphorsulfonic acid at 290.5 nm. The concentrations of the peptide stock solutions were determined by amino-acid analysis or by measuring tryptophan absorbance in 6 M Gdn HCl (assuming an extinction coefficient of 5600 $M^{-1}$ $cm^{-1}$ at 281 nm). Edelhoch, H. *Biochemistry* 1967, 6, 1948. Mean residue ellipticities (deg $cm^2$ $dmol^{-1}$) were calculated using the relation:

$$[\theta] = \theta_{obs} \times MRW/10lc \quad (1)$$

wherein $\theta_{obs}$ is the measured signal (ellipticity) in millidegrees, l is the optical pathlength of the cell in cm, c is concentration of the peptide in mg/mL and MRW is the mean residue molecular weight (molecular weight of the peptide divided by the number of residues).

Thermal denaturation studies were carried out at the concentrations indicated by monitoring the change in $[\theta]_{222}$ as a function of temperature. Temperature was increased in steps of 0.5° C. with an intervening equilibration time of 120s. Data was collected over 16 s per point. The $T_m$ was determined from the minima of the first derivative of $[\theta]_{222}$ with $T^{-1}$, where T is in K.

EXAMPLE 10

Analytical Ultracentrifugation

Apparent molecular masses were determined by sedimentation equilibrium on a Beckman XL-A ultracentrifuge. Loading peptide concentrations were 2–15 μM in 10 mM phosphate (pH 7.40), 137 mM NaCl, 2.7 mM KCl. The samples were centrifuged at 32 000 and 26 000 rpm for 18 hours at 10° C. before absorbance scans were performed.

Data obtained at 10° C. were fit globally to the following equation (2) that describes the sedimentation of a homogeneous species:

$$Abs = A' \exp(H \times M[x^2 - x_0^2]) + B \quad (2)$$

wherein Abs=absorbance at radius x, A'=absorbance at reference radius $x_0$, $H=(1-\bar{V}\rho)\omega^2/2RT$, $\bar{V}$=partial specific volume=0.758 mL/g, $\rho$=density of solvent=1.0017 g/mL, $\omega$=angular velocity in radians/sec, and M=apparent molecular weight, B=solvent absorbance (blank). We estimated partial specific volume using amino acid composition (Cohn, E. J., Edsall, J. T. *Proteins, Amino Acids and Peptides as Ions and Dipolar Ions*. New York, Reinhold, 1943) substituting leucine for hexafluoroleucine in the case of HF and FF for lack of available data.

EXAMPLE 11

Calculation of Free Energies

The thermodynamic cycle used for calculating $\Delta G_{spec}$ (free energy of specificity for the formation of homodimers) is depicted below. The superscripts U and F refer to the unfolded and folded states respectively of the disulfide bonded dimeric peptides.

$K_{redox}$ is the equilibrium constant for the redox reaction. $K_{random}$ is the equilibrium constant for the chance pairing of FF, HH and HF peptides and is assumed to be 2 as there are two equivalent ways for the formation of the heterodimer HF but only one way to form each homodimer. O'Shea, E. K.; Rutkowski, R.; Kim, P. S. *Cell* 1992, 68, 69–708. $FFFF^F$ is the dimer of the disulfide bonded dimer FF and $K_{tetramer}$ is the equilibrium constant for it's formation. $K_{redox}$ was estimated from equilibrium ratios of HH, FF and HF.

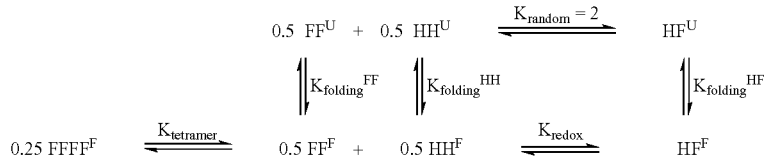

$$K_{redox} = \frac{[HF^F]}{[FF^F]^{0.5}[HH^F]^{0.5}}$$

$\Delta G_{spec}$(for homodimers)=$-\{\Delta G_{redox} + RT \ln 2\}$

EXAMPLE 12

Calculation of Free Energy of Unfolding for Homomdimer

The free energy of unfolding for HH was determined by assuming a two state equilibrium between folded and unfolded states:

where $F_{HH}$ is the folded species and $U_{HH}$ represents the fully unfolded HH. Data were obtained by monitoring $[\theta]_{222}$ as a function of Gdn HCl concentration. Data were analyzed by the linear extrapolation method to yield the free energy of unfolding. The equilibrium constant and therefore $\Delta G°$ are easily determined from the average fraction of unfolding. Assuming that the linear dependence of $\Delta G°$ with denaturant concentration in the transition region continues to zero concentration, the data can be extrapolated to obtain $\Delta G^*_{H_2O}{}^\circ$, the free energy difference in the absence of denaturant. Pace, C. N. *Methods in Enzymol.* 1995, 259, 538–554; and Tanford, C. *Adv. Protein Chem.* 1962, 17, 69–165.

Sedimentation equilibrium experiments suggest FF is a tetramer (dimer of the disulfide bonded dimer) in the 2–15 μM concentration range. Therefore, we used a unfolded monomer-folded dimer equilibrium to calculate $\Delta G^\circ$ of unfolding:

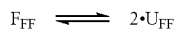

where $K_d = [U_{FF}]^2/[F_{FF}]$ ($U_{FF}$=unfolded FF and $F_{FF}$=folded dimer of FF with 4 helices). Since the total peptide concentration $P_t$, can be given by $P_t = 2 [F_{FF}] + [U_{FF}]$, the observed CD signal $Y_{obs}$ can be described in terms of folded and unfolded baselines, $Y_{fol}$ and $Y_{unfol}$, respectively by the following expression.

$$Y_{obs} = (Y_{unfol} - Y_{fol}) \frac{\sqrt{K_d^2 + 8K_d P_1} - K_d}{4P_1} + Y_{fol} \quad (2)$$

Additionally, $K_d$ can be expressed in terms of the free energy of unfolding.

$$K_d = \exp(-\Delta G^\circ / RT) \quad (3)$$

Assuming that the apparent free energy difference between folded $F_{FF}$ and unfolded $U_{FF}$ states is linearly dependent on the Gdn HCl concentration, $\Delta G^\circ$ can be written as:

$$\Delta G^\circ = \Delta G^*_{H_2O}{}^\circ - m[Gdn.HCl] \quad (4)$$

where $\Delta G^*_{H_2O}{}^\circ$ is the free energy difference in the absence of denaturant and m is the dependency of the unfolding transition with respect to the concentration of Gdn HCl. The data was fit for two parameters, $\Delta G^*_{H_2O}{}^\circ$, and m by nonlinear least squares fitting.

EXAMPLE 13

N-Boc-4,4,4-trifluorovalinol (2)

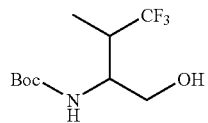

To a suspension of Boc-DL-trifluorovaline (1.30 g, 4.79 mmol) and NaHCO$_3$ (1.21 g, 14.37 mmol) in 20 mL of dry DMF was added 0.33 mL of CH$_3$I (5.27 mmol) at room temperature under argon. The resulting mixture was stirred for 5 h and then partitioned between 75 mL of ethyl acetate and 50 mL of water. The organic layer was washed with water (3×50 mL), dried over MgSO$_4$, and concentrated to yield 1.36 g (95%) of the Boc-DL-trifluorovaline methyl ester as a pale-yellow oil.

The Boc-TFV methyl ester (855 mg, 3 mmol) was dissolved in 20 mL of methanol, and NaBH4 (681 mg, 18 mmol) was added in small portions at 0° C. The reaction mixture was stirred overnight at room temperature and then diluted with 80 mL of ethyl acetate, washed with water (3×50 mL), and dried over MgSO$_4$. After removal of the solvent, the crude product (Boc-trifluorovalinol) was chromatographed on a silica gel column (silica gel, 300 g) using n-pentane/Et$_2$O (1:1) as eluant to give 452 mg of 2a as a pale-yellow solid (58%) and 214 mg of 2b as a white solid (28%).

(2S,3S)-, (2R,3R)-N-Boc-4,4,4-trifluorovalinol (2a)

$^1$H NMR (300 MHz, CDCl$_3$) δ 5.04 (d, 1H, J=9.3 Hz), 4.02 (m, 1H), 3.62 (m, 3H), 2.61 (m, 1H), 1.44 (s, 9H), 1.15 (d, 3H, J=7.2 Hz); $^{13}$C NMR (75.5 MHz, CDCl$_3$) δ 156.20 (C=O), 127.83 (q, CF$_3$, $^1J_{CF}$=279.9 Hz), 80.26 (C), 62.78 (CH$_2$), 51.09 (CH), 38.47 )q, CH, $^2J_{CF}$=25.6 Hz), 28. 40 (3×CH$_3$), 8.76 (CH$_3$); $^{19}$F NMR (282.6 MHz, CDCl$_3$/CFCl$_3$) δ −70.63 (d, 3F, J=9.0 Hz); FT-IR (KBr pellet, v$_{max}$, cm$^{-1}$) 3435s, 3300s, 2990s, 2979m, 2954m, 1691s, 1539s, 1537s, 1265s, 1172s, 1125; GC-MS (Cl, CH$_4$): 258 (14, [M+1]$^+$), 242 (4), 202 (100), 158 (37), 57 (14).

(2S,3R)-, (2R,3S)-N-Boc-4,4,4-trifluorovalinol (2b)

$^1$H NMR (300 MHz, CDCl$_3$) δ 5.11 (d, 1H, J=8.4 Hz), 3.80 (m, 1H), 3.66 (m, 2H), 3.45 (t, 1H, J=5.7 Hz), 2.53 (m, 1H), 1.42 (s, 9H), 1.15 (d, 3H, J=7.2 Hz); $^{13}$C NMR (75.5 MHz, CDCl$_3$) δ 156.43 (C=O), 127.91 (q, CF$_3$, $^1J_{CF}$=280.2 Hz), 80.30 (C), 62.92 (CH$_2$), 52.56 (CH), 38.89 (q, CH, $^2J_{CF}$=24.8 Hz), 28. 40 (3 ÅCH$_3$), 10.59 (CH$_3$); $^{19}$F NMR (282.6 MHz, CDCl$_3$/CFCl$_3$) δ −68.76 (d, 3F, J=8.5 Hz); FT-IR (film, v$_{max}$ cm$^{-1}$): 3436s, 3302s, 3012m, 2990m, 2954m, 1691s, 1532s, 1265s, 1172s, 1127s; GC-MS (Cl, CH$_4$): 258 (14, [M+1]$^+$), 242 (4), 202 (100), 182 (8), 57 (14).

EXAMPLE 14

(2S,3S)-, (2R,3R)-N-Ac-4,4,4-trifluorovaline (3a)

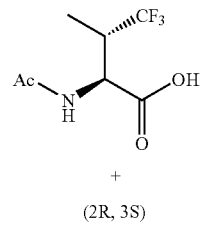

A solution of alcohol 2a (257 mg, 1 mmol) in 4 mL of dry DMF was treated with PDC (2.26 g, 6 mmol) at room temperature under argon and stirred overnight. The reaction mixture was then diluted with 20 mL of diethyl ether/30 mL of saturated NaHCO$_3$ solution. The organic layer was washed with 10 mL of saturated NaHCO$_3$. The combined aqueous layers were acidified to pH 2 with 3 N HCl and extracted with diethyl ether (2×50 mL). The combined organic layers were dried over MgSO$_4$ and concentrated to yield 176 mg of the corresponding Boc-trifluorovaline (65%).

Boc-TFV (176 mg, 0.65 mmol) was treated with 4 mL of 40% trifluoroacetic acid in CH$_2$Cl$_2$ for 10 min. After removal of the solvent, the residue was dissolved in 2 mL of water, treated with NaOH (260 mg, 6.5 mmol) at 0° C., followed by dropwise addition of acetic anhydride (0.13 mL, 1.3 mmol). The reaction mixture was stirred at 0° C. for 30 min before it was allowed to warm to room temperature.

After stirring for another 1.5 h, the mixture was diluted with 10 mL of water, acidified to pH 2 with 1 N HCl, and extracted with ethyl acetate (2×60 mL). The combined organic layers were dried over $MgSO_4$ and concentrated to give the desired product 3a as a white solid (132 mg, 95%). $^1$H NMR (300 MHz, $D_2O$) δ 4.96 (d, 1H, J=3.0 Hz), 3.07 (m, 1H), 2.04 (s, 3H), 1.15 (d, 3H, J=7.2 Hz); $^{19}$F NMR (282.6 MHz, $D_2O/CF_3CO_2H$) δ −71.63 (d, 3F, J=8.8 Hz); FT-IR (KBr pellet, $v_{max}$, $cm^{-1}$) 3397s (br), 3253s, 3068m, 2981s, 2948m, 1686s, 1552s, 1369s, 1289s, 1174s, 1145s, 1055s; GC-MS (CI, $CH_4$): 214 (100, $[M+1]^+$), 196 (9), 172 (33), 82 (33), 57 (6).

(2S,3R)-, (2R,3S)-N-Ac-4,4,4-trifluorovaline (3b)

$^1$H NMR (300 MHz, $D_2O$) δ 4.67 (d, 1H, J=3.3 Hz), 3.07 (m, 1H), 2.04 (s, 3H), 1.17 (d, 3H, J=7.2 Hz); $^{19}$F NMR (282.6 MHz, $D_2O/CF_3CO_2H$) δ −69.43 (d, 3F, J=8.8 Hz); FT-IR (KBr pellet, $v_{max}$, $cm^{-1}$) 3397s (br), 3253s, 3068m, 2981s, 2948m, 1686s, 1552s, 1369s, 1289s, 1174s, 1145s, 1055s; GC-MS (CI, $CH_4$): 214 (100, $[M+1]^+$), 196 (9), 172 (33), 101 (10), 82 (33), 57 (6).

EXAMPLE 15

(2S,3S)-4,4,4-Trifluorovaline (4a)

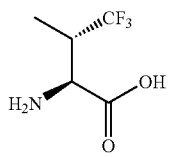

4a

To a solution of 3a (107 mg, 0.5 mmol) in 1 mL of pH 7.9 aq. LiOH/HOAc was added porcine kidney acylase I (10 mg) at 25° C. The mixture was stirred at 25° C. for 48 h (pH was maintained at 7.5 by periodic addition of 1 N LiOH). The reaction was then diluted with 5 mL of water, acidified to pH 5.0, heated to 60° C. with Norit, and filtered. The filtrate was acidified to pH 1.5 and extracted with ethyl acetate (2×10 mL). The aqueous layer was freeze-dried to give 49 mg of 4a (95%). The combined organic layers were concentrated, and the residue refluxed in 3 N HCl for 6 h, then freeze-dried to yield 50 mg of 4c (98%).

The other two diastereomers, 4b and 4d, were obtained from 3b using the same procedure.

(2S,3S)-4,4,4-Trifluorovaline (4a)

$^1$H NMR (300 MHz, $D_2O$) δ 4.24 (dd, 1H, J=2.1, 3.9 Hz), 3.23 (m, 1H), 1.30 (d, 3H, J=7.2 Hz); $^{19}$F NMR (282.6 MHz, $D_2O/CF_3CO_2H$) δ −71.69 (d, 3F, J=9.3 Hz); $[\alpha]_D^{23.7}$=+7.2° (c 0.75, 1 N HCl).

(2S,3R)-4,4,4-Trifluorovaline (4b)

$^1$H NMR (300 MHz, $D_2O$) δ 4.35 (t, 1H, J=2.7 Hz), 3.27 (m, 1H), 1.22 (d, 3H, J=7.5 Hz); $^{19}$F NMR (282.6 MHz, $D_2O/CF_3CO_2H$) δ −70.04 (d, 3F, J=9.0 Hz); $[\alpha]_D^{23.3}$=+12.8° (c 0.5, 1 N HCl).

(2R,3R)-4,4,4-Trifluorovaline (4c)

$^1$H NMR (300 MHz, $D_2O$) δ 4.24 (dd, 1H, J=2.1, 3.9 Hz), 3.23 (m, 1H), 1.30 (d, 3H, J=7.2 Hz); $^{19}$F NMR (282.6 MHz, $D_2O/CF_3CO_2H$) δ −70.04 (d, 3F, J=9.0 Hz).

(2R,3S)-4,4,4-Trifluorovaline (4d)

$^1$H NMR (300 MHz, $D_2O$) δ 4.35 (t, 1H, J=2.7 Hz), 3.27 (m, 1H), 1.22 (d, 3H, J=7.5 Hz); $^{19}$F NMR (282.6 MHz, $D_2O/CF_3CO_2H$) δ −71.69 (d, 3F, J=9.3 Hz).

EXAMPLE 16

N-Boc-5,5,5-trifluoroleucine methyl ester (6)

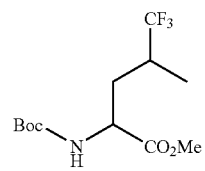

6

A mixture of Boc-DL-trifluoroleucine (1.25 g, 4.38 mmol), iodomethane (0.3 mL, 4.82 mmol), $NaHCO_3$ (1.1 g, 13.15 mmol), and dry DMF (20 mL) was stirred at room temperature under argon for 6 h, then diluted with 200 mL of ethyl acetate, and washed with water (4×100 mL). The organic layer was dried over $Na_2SO_4$ and concentrated to give 1.25 g of product as a pale-yellow oil (95%). Column chromatography on silica gel (500 g) using $Et_2O$/n-pentane (1:4) as eluant afforded 420 mg of (2S,4R)-, (2R,4S)-N-Boc-5,5,5-trifluoroleucine methyl ester (6a) (32%), 347 mg of (2S,4S)-, (2R,4R)-N-Boc-5,5,5-trifluoroleucine methyl ester (6b) (27%), and 337 mg of the mixture of 6a and 6b (26%).

(2S,4R)-, (2R,4S)-N-Boc-5,5,5-trifluoroleucine methyl ester (6a)

$^1$H NMR (300 MHz, $CDCl_3$) δ 5.29 (d, 1H, J=6.9 Hz), 4.32 (m, 1H), 3.70 (s, 3H), 2.31 (m, 1H), 2.12 (m, 1H), 1.58 (m, 1H), 1.37 (s, 9H), 1.11 (d, 3H, J=6.9 Hz); $^{13}$C NMR (75.5 MHz, $CDCl_3$) δ 172.72 (C=O), 155.29 (C=O), 128.09 (q, $CF_3$, $^1J_{CF}$=278.9 Hz), 80.27 (C), 52.54 ($CH_3$), 51.70 (CH), 35.13 (q, CH, $^2J_{CF}$=26.4 Hz), 32.98 ($CH_2$), 28.30 (3×$CH_3$), 13.17 ($CH_3$); $^{19}$F NMR (282.6 MHz, $CDCl_3/CFCl_3$) δ −74.15 (d, 3F, J=8.2 Hz); FT-IR (film, $v_{max}$ $cm^{-1}$) 3360m, 2984m, 2938m, 1747s, 1716s, 1520s, 1368s, 1269s, 1168s, 1133m; GC-MS (CI, $CH_4$): 300 (2, $[M+1]^+$), 284 (7), 244 (100), 200 (66), 82 (21), 57 (24).

(2S,4S)-, (2R,4R)-N-Boc-5,5,5-trifluoroleucine methyl ester (6b)

$^1$H NMR (300 MHz, $CDCl_3$) δ 5.02 (d, 1H, J=8.7 Hz), 4.38 (m, 1H), 3.76 (s, 3H), 2.32 (m, 1H), 1.91–1.74 (br. m, 2H), 1.44 (s, 9H), 1.20 (d, 3H, J=6.9 Hz); $^{13}$C NMR (75.5 MHz, $CDCl_3$) δ 173.03 (C=O), 155.86 (C=O), 128.24 (q, $CF_3$, $^1J_{CF}$=278.9 Hz), 80.57 (C), 52.80 ($CH_3$), 50.83 (CH), 35.02 (q, CH, $^2J_{CF}$=26.9 Hz), 33.00 ($CH_2$), 28.42 (3×$CH_3$), 12.28 ($CH_3$); $^{19}$F NMR (282.6 MHz, $CDCl_3/CFCl_3$) δ −74.03 (d, 3F, J=8.7 Hz); FT-IR (KBr pellet, $v_{max}$, $cm^{-1}$) 3368s, 3014m, 2983m, 2961m, 1763s, 1686s, 1527s, 1265s, 1214s, 1170s, 1053s, 1028s; GC-MS (CI, $CH_4$): 300 (2, $[M+1]^+$), 284 (7), 244 (100), 224 (30), 200 (66), 57 (24).

EXAMPLE 17

(2S,4R)-, (2R,4S)-N-Ac-5,5,5-trifluoroleucine (7a)

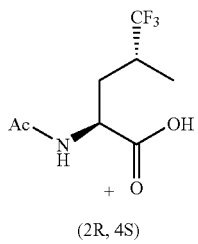

(2R, 4S)

(2S,4R)-, (2R,4S)-N-Boc-5,5,5-trifluoroleucinol

To a solution of 6a (420 mg, 1.4 mmol) in methanol (10 mL) was added NaBH$_4$ (531 mg, 14.0 mmol) in small portions. The reaction mixture was stirred at room temperature for 1 h before removal of the solvent. The residue was partitioned between 100 mL of ethyl acetate and 50 mL of water. The aqueous layer was extracted with 100 mL of ethyl acetate. The combined organic layers were dried over Na$_2$SO$_4$ and concentrated to yield 357 mg of the desired product as a white solid (94%). $^1$H NMR (300 MHz, CDCl$_3$) δ 4.74 (m, 1H), 3.71 (m, 2H), 3.58 (m, 1H), 2.31 (m, 1H), 2.14 (m, 1H), 1.92 (m, 1H), 14.5 (s, 9H), 1.17 (d, 3H, J=7.0 Hz). $^{13}$C NMR (75.5 MHz, CDCl$_3$) δ 156.26 (C=O), 128.41 (q, CF$_3$, $^1J_{CF}$=279.4 Hz), 80.14 (C), 64.78 (CH$_2$), 50.73 (CH), 35.59 (q, CH, $^2J_{CF}$=29.6 Hz), 31.74 (CH$_2$), 28.52 (3×CH$_3$), 13.71 (CH$_3$); $^{19}$F NMR (282.6 MHz, CDCl$_3$/CFCl$_3$) δ −73.84 (br. s, 3F); GC-MS (CI, CH$_4$): 272 (100, [M+1]$^+$), 216 (68), 172 (26), 57 (11).

(2S,4S)-, (2R,4R)-N-Boc-5,5,5-trifluoroleucinol $^1$H NMR (300 MHz, CDCl$_3$) δ 4.58 (m, 1H), 3.79 (m, 1H), 3.68 (m, 1H), 3.58 (m, 1H), 2.27 (m, 1H), 2.05 (m, 1H), 1.80 (m, 1H), 1.45 (s, 9H), 1.18 (d, 3H, J=6.6 Hz). $^{13}$C NMR (75.5 MHz, CDCl$_3$) δ 156.47 (C=O), 128.56 (q, CF$_3$, $^1J_{CF}$=278.7 Hz), 80.20 (C), 66.31 (CH$_2$), 49.49 (CH), 35.15 (q, CH, $^2J_{CF}$=26.7 Hz), 31.71 (CH$_2$), 28.50 (3×CH$_3$), 12.56 (CH$_3$); $^{19}$F NMR (282.6 MHz, CDCl$_3$/CFCl$_3$) δ −73.98 (d, 3F, J=8.5 Hz); GC-MS (CI, CH$_4$): 272 (100, [M+1]$^+$), 172 (26), 57 (11).

(2S,4R)-, (2R,4S)-N-Ac-5,5,5-trifluoroleucine (7a)

A mixture of (2S,4R)-, (2R,4S)-N-Boc-5,5,5-trifluoroleucinol (330 mg, 1.23 mmol), PDC (4.62 g, 12.3 mmol), and dry DMF (2.5 mL) was stirred at room temperature under argon for 4 h, then diluted with 50 mL of ethyl acetate and 50 mL of water. The organic layer was washed with 30 mL of 1N HCl and 2×30 mL of water, dried over MgSO$_4$, and concentrated to give 198 mg of (2S,4R)-, (2R,4S)-N-Boc-5,5,5-trifluoroleucine as a pale-brownish oil (60%).

A solution of the above product (180 mg, 0.63 mmol) in 2 mL of CH$_2$Cl$_2$ was treated with 0.5 mL of trifluoroacetic acid for 30 min at room temperature. After removal of the solvent, the yellowish residue was dissolved in 2 mL of water, treated with NaOH (126 mg, 3.15) at 0° C., and acetic anhydride (0.12 mL, 1.26 mmol) was then added dropwise. The reaction mixture was stirred at 0° C. for 30 min, then allowed to warm to room temperature. After stirring for another 1 h, the mixture was diluted with 30 mL of water, acidified to pH 2 with 3 N HCl, and extracted with ethyl acetate (2×90 mL). The combined organic layers were dried over Na$_2$SO$_4$ and concentrated to yield 136 mg of 7a as a white solid (95%). $^1$H NMR (300 MHz, D$_2$O) δ 4.48 (dd, 1H, J=6.1, 8.8 Hz), 2.51 (m, 1H), 2.27 (m, 1H), 2.06 (s, 3H), 1.79 (m, 1H), 1.18 (d, 3H, J=7.0 Hz); $^{13}$C NMR (75.5 MHz, D$_2$O) δ 175.48 (C=O), 174.60 (C=O), 128.53 (q, CF$_3$, $^1J_{CF}$=278.9 Hz), 51.24 (CH), 34.88 (q, CH, $^2J_{CF}$=26.6 Hz), 31.21 (CH$_2$), 21.90 (CH$_3$), 13.03 (CH$_3$); $^{19}$F NMR (282.6 MHz, D$_2$O/CF$_3$CO$_2$H) δ −73.68 (d, 3F, J=9.0 Hz); FT-IR (KBr pellet, v$_{max}$, cm$^{-1}$) 3343s, 3063–2487m (br.), 2932m, 2894m, 1709s, 1613s, 1549s, 1266s, 1179s, 1137s; GC-MS (CI, CH$_4$): 228 (100, [M+1]$^+$), 211 (47), 186 (26), 140 (16), 57 (11).

(2S,4S)-, (2R,4R)-N-Ac-5,5,5-trifluoroleucine (7b)

$^1$H NMR (300 MHz, D$_2$O) δ 4.48 (dd, 1H, J=3.8, 11.6 Hz), 2.41 (m, 1H), 2.07 (s, 3H), 2.15–1.91 (br. m, 2H), 1.16 (d, 3H, J=6.9 Hz); $^{13}$C NMR (75.5 MHz, D$_2$O) δ 178.35 (C=O), 177.38 (C=O), 131.09 (q, CF$_3$, $^1J_{CF}$=278.3 Hz), 52.72 (CH), 37.31 (q, CH, $^2J_{CF}$=26.6 Hz), 33.06 (CH$_2$), 24.50 (CH$_3$), 13.90 (CH$_3$); $^{19}$F NMR (282.6 MHz, D$_2$O/CF$_3$CO$_2$H) δ −73.87 (d, 3F, J=8.5 Hz); FT-IR (KBr pellet, v$_{max}$, cm$^{-1}$) 3336s, 2977m, 2949m, 2897m, 2615m, 2473s, 1711s, 1628s, 1551s, 1276s, 1250s, 1127s, 1095s; GC-MS (CI, CH$_4$): 228 (100, [M+1]$^+$), 211 (47), 186 (26), 140 (16), 120 (3), 57 (11).

EXAMPLE 18

(2S,4R)-5,5,5-Trifluoroleucine (8a)

To a solution of 7a (136 mg, 0.6 mmol) in 2 mL of pH 7.9 aqueous LiOH/HOAc was added porcine kidney acylase I (18 mg) at 27° C. The mixture was stirred at 27° C. for 48 h (pH was maintained at 7.5 by periodic addition of 1 N LiOH). It was further diluted with 5 mL of water, acidified to pH 5.0, heated to 60° C. with Norit, and filtered. The filtrate was acidified to pH 1.5 and extracted with ethyl acetate (2×50 mL). The aqueous layer was freeze-dried to give 63 mg of 8a (95%). The combined organic layers were concentrated, and the residue refluxed in 3 N HCl for 6 h, then freeze-dried to yield 64 mg of 8c (96%).

The other two diastereomers, 8b and 8d, were obtained from 7b using the same procedure.

(2S,4R)-5,5,5-Trifluoroleucine (8a)

$^{19}$F NMR (282.6 MHz, D$_2$O/CF$_3$CO$_2$H) δ −74.33 (d, 3F, J=9.0 Hz); [α]$_D^{22.9}$=+21.6° (c 0.5, 1N HCl).

(2S,4S)-5,5,5-Trifluoroleucine (8b)

$^{19}$F NMR (282.6 MHz, D$_2$O/CF$_3$CO$_2$H) δ −74.11 (d, 3F, J=8.2 Hz); [α]$_D^{23.6}$=−4.0° (c 0.8, 1N HCl).

(2R,4S)-5,5,5-Trifluoroleucine (8c)

$^{19}$F NMR (282.6 MHz, D$_2$O/CF$_3$CO$_2$H) δ −74.33 (d, 3F, J=9.0 Hz).

(2R,4R)-5,5,5-Trifluoroleucine (8d)

$^{19}$F NMR (282.6 MHz, D$_2$O/CF$_3$CO$_2$H) δ −74.11 (d, 3F, J=8.2 Hz).

EXAMPLE 19

Boc-TFV(2S,3S)-Ser(Ot-Bu)-OMe(2S)

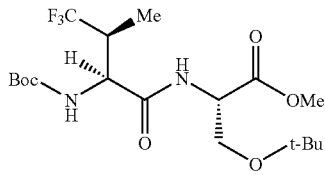

To a stirred solution of (2S,4S)-5,5,5-Trifluorovaline (4b) (5 mg, 0.02 mmol) in DMF (1 mL) was added diisopropylethyl amine (DIEA, 0.01 mL, 0.06 mmol), O-(benzotriazol-1-yl)-N,N,N',N'-tetramethyluronium hexafluorophosphate (HBTU, 8 mg, 0.02 mmol), and the HCl salt of (2S)-H-Ser(Ot-Bu)-OMe (9 mg, 0.04 mmol), sequentially. The mixture was stirred at room temperature for 20 min before dilution with water (5 mL) and extraction with diethyl ether (15 mL). The organic layer was washed with 1 N HCl (2×5 mL) and 5% $NaHCO_3$ (2×8 mL), dried over $MgSO_4$, and concentrated to give 7 mg of the dipeptide (88%). $^1H$ NMR (300 MHz, $CDCl_3$) δ 6.92 (d, 1H, J=7.8 Hz), 5.16 (d, 1H, J=8.7 Hz), 4.65 (m, 1H), 4.39 (dd, 1H, J=5.1, 8.8 Hz), 3.81 (dd, 1H, J=2.7, 9.0 Hz), 3.74 (s, 3H), 3.56 (dd, 1H, J=3.0, 9.0 Hz), 3.04 (m, 1H), 1.46 (s, 9H), 1.23 (d, 3H, J=7.2 Hz), 1.14 (s, 9H); $^{19}F$ NMR (282.6 MHz, $CDCl_3/CFCl_3$) δ −68.57 (d, 3F, J=8.7 Hz).

Boc-TFV(2S,3R)-Ser(Ot-Bu)-OMe(2S)
$^{19}F$ NMR (282.6 MHz, $CDCl_3/CFCl_3$) δ −71.36 (d, 3F, J=7.9 Hz).

Boc-TFV(2R,3S)-Ser(Ot-Bu)-OMe(2S)
$^{19}F$ NMR (282.6 MHz, $CDCl_3/CFCl_3$) δ −71.48 (d, 3F, J=8.5 Hz).

Boc-TFV(2R,3R)-Ser(Ot-Bu)-OMe(2S)
$^{19}F$ NMR (282.6 MHz, $CDCl_3/CFCl_3$) δ −68.49 (d, 3F, J=9.0 Hz).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A compound represented by A:

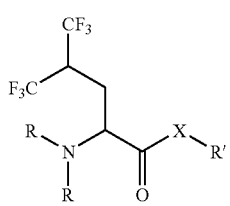

wherein
X represents O, S, $N(R^2)$, or $C(R^3)_2$;
R represents independently for each occurrence H, alkyl, aryl, heteroaryl, heteroaralkyl, formyl, acyl, alkoxycarbonyl, aralkoxycarbonyl, alkylaminocarbonyl, or aralkylaminocarbonyl;
$R^2$ represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;
$R^3$ represents independently for each occurrence H, alkyl, aryl, heteroaryl, aralkyl, heteroaralkyl, formyl, acyl, alkoxycarbonyl, aralkoxycarbonyl, alkylaminocarbonyl, or aralkylaminocarbonyl;
R' represents H, alkyl, aryl, heteroaryl, aralkyl, or heteroaralkyl; or XR' represents halide;
the stereochemical configuration at any stereocenter of a compound represented by A may be R, S, or a mixture of these configurations; and
the enantiomeric excess of a compound represented by A is greater than or equal to about 95%.

2. The compound of claim 1, wherein X represents O or $N(R^2)$.

3. The compound of claim 1, wherein R represents independently for each occurrence H, alkyl, acyl, alkoxycarbonyl, aralkoxycarbonyl, alkylaminocarbonyl, or aralkylaminocarbonyl; $R^2$ represents independently for each occurrence H, alkyl, aralkyl, acyl, alkoxycarbonyl, aralkoxycarbonyl, or aralkylaminocarbonyl; and $R^3$ represents independently for each occurrence H, alkyl, aralkyl, acyl, alkoxycarbonyl, aralkoxycarbonyl, or aralkylaminocarbonyl.

4. The compound of claim 1, wherein R, $R^2$ and $R^3$ represent independently for each occurrence H.

5. The compound of claim 1, wherein R' represents H, alkyl, or aralkyl.

6. The compound of claim 1, wherein R' represents H.

7. The compound of claim 1, wherein R, $R^2$ and $R^3$ represent independently for each occurrence H; and R' represents H.

8. The compound of claim 1, wherein X represents O or $N(R^2)$; R represents independently for each occurrence H, alkyl, acyl, alkoxycarbonyl, aralkoxycarbonyl, alkylaminocarbonyl, or aralkylaminocarbonyl; $R^2$ represents independently for each occurrence H, alkyl, aralkyl, acyl, alkoxycarbonyl, aralkoxycarbonyl, alkylaminocarbonyl, or aralkylaminocarbonyl; and $R^3$ represents independently for each occurrence H, alkyl, aralkyl, acyl, alkoxycarbonyl, aralkoxycarbonyl, alkylaminocarbonyl, or aralkylaminocarbonyl.

9. The compound of claim 1, wherein X represents O or $N(R^2)$; and R and $R^2$ represent independently for each occurrence H.

10. The compound of claim 1, wherein X represents O or $N(R^2)$; and R' represents H, alkyl, or aralkyl.

11. The compound of claim 1, wherein X represents O or $N(R^2)$; and R' represents H.

12. The compound of claim 1, wherein X represents O or $N(R^2)$; R represents independently for each occurrence H, alkyl, acyl, alkoxycarbonyl, aralkoxycarbonyl, alkylaminocarbonyl, or aralkylaminocarbonyl; $R^2$ represents independently for each occurrence H, alkyl, aralkyl, acyl, alkoxycarbonyl, aralkoxycarbonyl, alkylaminocarbonyl, or aralkylaminocarbonyl; and R' represents H, alkyl, or aralkyl.

13. The compound of claim 1, wherein X represents O or $N(R^2)$; R, and $R^2$ represent independently for each occurrence H; and R' represents H, alkyl, or aralkyl.

14. The compound of claim 1, wherein X represents O or N($R^2$); R represents independently for each occurrence H, alkyl, acyl, alkoxycarbonyl, aralkoxycarbonyl, alkylaminocarbonyl, or aralkylaminocarbonyl; $R^2$ represents independently for each occurrence H, alkyl, aralkyl, acyl, alkoxycarbonyl, aralkoxycarbonyl, alkylaminocarbonyl, or aralkylaminocarbonyl; and R' represents H.

15. The compound of claim 1, wherein X represents O or N($R^2$); R, and $R^2$ represent independently for each occurrence H; and R' represents H.

16. The compound of claim 1, wherein said compound is a single stereoisomer.

17. The compound of claim 1, wherein said compound is in the form of a salt.

18. A formulation, comprising a compound of claim 1 and a pharmaceutically acceptable excipient.

19. The compound of claim 2, wherein said compound is a single stereoisomer.

20. The compound of claim 3, wherein said compound is a single stereoisomer.

21. The compound of claim 4, wherein said compound is a single stereoisomer.

22. The compound of claim 5, wherein said compound is a single stereoisomer.

23. The compound of claim 6, wherein said compound is a single stereoisomer.

24. The compound of claim 7, wherein said compound is a single stereoisomer.

25. The compound of claim 8, wherein said compound is a single stereoisomer.

26. The compound of claim 9, wherein said compound is a single stereoisomer.

27. The compound of claim 10, wherein said compound is a single stereoisomer.

28. The compound of claim 11, wherein said compound is a single stereoisomer.

29. The compound of claim 12, wherein said compound is a single stereoisomer.

30. The compound of claim 13, wherein said compound is a single stereoisomer.

31. The compound of claim 14, wherein said compound is a single stereoisomer.

32. The compound of claim 15, wherein said compound is a single stereoisomer.

* * * * *